United States Patent
Hakim et al.

(10) Patent No.: US 10,758,482 B2
(45) Date of Patent: Sep. 1, 2020

(54) IMMUNOMODULATING TREATMENTS OF BODY CAVITIES

(71) Applicant: UROGEN PHARMA LTD., Ra'anana (IL)

(72) Inventors: Gil Hakim, Ra'anana (IL); Dalit Strauss-Ayali, Sde Warburg (IL); Astar Friedman, Petah Tikva (IL); Marina Konorty, Herzilya (IL)

(73) Assignee: UROGEN PHARMA LTD., Raanana (IL)

( * ) Notice: Subject to any disclaimer, the term of this patent is extended or adjusted under 35 U.S.C. 154(b) by 0 days.

(21) Appl. No.: 16/297,839

(22) Filed: Mar. 11, 2019

(65) Prior Publication Data

US 2019/0201334 A1    Jul. 4, 2019

Related U.S. Application Data

(63) Continuation-in-part of application No. PCT/IL2017/051164, filed on Oct. 25, 2017.

(60) Provisional application No. 62/412,482, filed on Oct. 25, 2016.

(51) Int. Cl.
| | |
|---|---|
| *A61K 9/06* | (2006.01) |
| *A61K 47/34* | (2017.01) |
| *A61P 35/00* | (2006.01) |
| *A61K 39/395* | (2006.01) |
| *C07K 16/28* | (2006.01) |
| *A61K 9/00* | (2006.01) |
| *A61K 31/4745* | (2006.01) |
| *A61K 31/55* | (2006.01) |
| *A61K 31/437* | (2006.01) |

(Continued)

(52) U.S. Cl.
CPC .............. *A61K 9/06* (2013.01); *A61K 9/0019* (2013.01); *A61K 31/437* (2013.01); *A61K 31/4745* (2013.01); *A61K 31/55* (2013.01); *A61K 39/3955* (2013.01); *A61K 47/34* (2013.01); *A61K 47/36* (2013.01); *A61P 35/00* (2018.01); *C07K 16/2818* (2013.01); *C07K 16/2827* (2013.01); *A61K 2039/505* (2013.01); *A61K 2039/545* (2013.01); *C07K 2317/21* (2013.01); *C07K 2317/24* (2013.01); *C07K 2317/76* (2013.01)

(58) Field of Classification Search
None
See application file for complete search history.

(56) References Cited

FOREIGN PATENT DOCUMENTS

| WO | 2011089604 | * | 7/2011 |
| WO | 2015168379 | | 11/2015 |

(Continued)

OTHER PUBLICATIONS

Pal et al., Designed Monomers and Polymers 12 (2009) 197-220 (Year: 2009).*

(Continued)

*Primary Examiner* — Karl J Puttlitz
(74) *Attorney, Agent, or Firm* — JMB Davis Ben-David

(57) ABSTRACT

Described herein are compositions and methods for treating cancer of a body cavity, specifically urinary tract cancer, by way of a combination of at least two immunomodulatory agents, wherein one or more of the therapeutic agents are embedded in, and slowly released from, a biocompatible hydrogel composition.

15 Claims, 9 Drawing Sheets
(7 of 9 Drawing Sheet(s) Filed in Color)

(51) Int. Cl.
A61K 47/36 (2006.01)
A61K 39/00 (2006.01)

(56) References Cited

FOREIGN PATENT DOCUMENTS

| WO | 2016004213 | * | 1/2016 |
| WO | 2016146261 | * | 9/2016 |

OTHER PUBLICATIONS

Gandra, The Preparation and Characterization of Poloxamer-Based Temperature-Sensitive Hydrogels for Topical Drug Delivery, Thesis, 2013 (Year: 2013).*

Mangsbo et al, "Enhanced Tumor Eradication by Combining CTLA-4 or PD-1 Blockade With CpG Therapy", Journal of Immunotherapy, vol. 33, Nr:3, pp. 225-235, 2010.

Smith et al. "Future directions in bladder cancer immunotherapy: towards adaptive immunity", Immunotherapy, vol. 8, Nr:3, pp. 351-365, 2016.

Sasikala et al. "Abstract B041: An injectable magnetic nanogel system for for filling surgical residual cavity with affective cancer immunotherapy combined hyperthermic capability," Cancer Imm. Res, Feb. 1, 2019.

Park et al., "Extended release of perioperative immunotherapy prevents tumor recurrence and eliminates metastases," Science Translational Medicine, 10:1916, Mar. 21, 2018.

Chen et al, "Photothermal therapy with immune-adjuvent nanoparticles together with checkpoint blockade for effective aancer immunotherapy" Nature Communications, 7:1-13, Oct. 21, 2016.

* cited by examiner

IMMUNOMODULATING TREATMENTS OF BODY CAVITIES

CROSS REFERENCE TO RELATED APPLICATIONS

This is a Continuation-in-Part of International Patent Application No. PCT/IL2017/051164 filed Oct. 25, 2017; which in turn claims the benefit of U.S. Provisional Patent Application No. 62/412,482, filed Oct. 25, 2016. The contents of the foregoing patent applications are incorporated by reference herein in their entirety.

FIELD

Provided herein are compositions and methods for treating cancer of a body cavity, including urinary tract cancer, by way of a combination of at least two immunomodulatory agents, wherein one or more of the therapeutic agents are embedded in, and slowly released from, a biocompatible hydrogel composition.

BACKGROUND

Cancers are diseases of uncontrolled proliferation of abnormal cells. Urothelial carcinoma of the urinary bladder represents more than 90% of all bladder cancers, about 80% of which are non-muscle invasive bladder cancer (NMIBC), a form of superficial cancer. Transurethral resection and radical cystectomy remain the mainstay of treatment for NMIBC and MIBC (muscle invasive bladder cancer), respectively. Intravesical therapy with mitomycin is a preferred adjuvant therapy to surgery aiming at reducing disease recurrence and progression. However, some cancers remain refractory to current biological and chemotherapeutic treatments.

Certain combinations of immunomodulating compositions have been proposed to simultaneously activate innate and adaptive immunity to target tumors. However, toxicity from systemic administration of certain treatments (e.g. CTLA-4 antagonist antibodies) has limited their systemic applications for such treatments. Moreover, despite some early promise, at least one report has indicated that the benefit of such combinations may be limited (see for example International Patent Publication WO2016/23960).

Some immune response modulators have a relatively short half-life in terms of residence time at a given body cavity. It is known that such modulators appear to be cleared or metabolized, or simply diffuse away from a body cavity. This short residence duration may reduce the immune checkpoint modulator's ability to activate some immune system cells at the desired site.

There is thus a substantial ongoing need for new means of controlling the delivery and the activity of immune checkpoint modulators in order to expand their uses and therapeutic benefits.

SUMMARY

Provided herein is the discovery of a significant benefit from treating a cancer of a body cavity with a composition that includes a combination of TLR agonists and immune check point modulators (i.e. inducers or inhibitors) in a unique thermoreversible hydrogel composition. Such methods include treating cancer of an internal body cavity in a human subject by administering to a subject in need thereof a therapeutically effective amount of a TLR agonist, and an immune checkpoint modulator, wherein at least one of the TLR agonist and the immune checkpoint modulator are provided in a thermo-reversible hydrogel composition comprising chitosan or at least one tri block copolymer having a general formula ABA or BAB copolymer, wherein A is a hydrophilic block and B is a hydrophobic block, thereby treating the cancer of the body cavity.

Further described herein are methods for inhibiting regrowth of a cancer of an internal body cavity in a human subject by administering to a subject in need thereof a therapeutically effective amount of a TLR agonist, and an immune checkpoint modulator, wherein at least one of the TLR agonist and the immune checkpoint modulator are provided in a thermo-reversible hydrogel composition comprising chitosan or at least one tri block copolymer having a general formula ABA or BAB copolymer, wherein A is a hydrophilic block and B is a hydrophobic block, and wherein the TLR agonist and immune checkpoint modulator are administered to the subject subsequent to a treatment for the cancer which removed or decreased the amount of the cancer in the subject, thereby inhibiting cancer regrowth.

Additionally described herein are methods for treating a cancer of an internal body cavity in a subject by administering to a subject in need thereof (a) a therapeutically effective amount of a TLR agonist, and (b) a therapeutically effective amount of an immune checkpoint modulator selected from an anti-PD1, anti-PDL1, and anti-CTLA4 agent; wherein (a) and (b) are provided separately in a thermo-reversible hydrogel composition comprising a chitosan or tri block copolymer having a general formula ABA or BAB, wherein A is a hydrophilic block and B is a hydrophobic block, and administered locally into the internal body cavity.

Additionally provided herein are compositions including a TLR agonist, and an immune checkpoint modulator, wherein at least one of the TLR agonist and the immune checkpoint modulator (inhibitor or activator) are formulated in a thermo-reversible hydrogel composition comprising chitosan or at least one tri block copolymer having a general formula ABA or BAB copolymer, wherein A is a hydrophilic block and B is a hydrophobic block.

The foregoing and other objects, features, and advantages will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

3C) for T-cell populations stratified by treatment group. Symbols indicate significant differences, p<0.05 Kruskal-Wallis test.

Figures 4A, 4B, 4C:
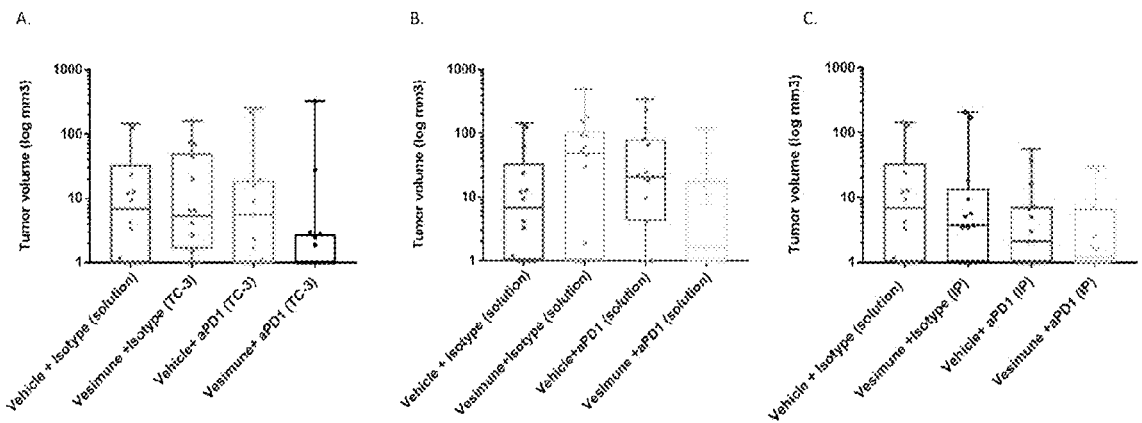

FIGS. 4A-4C show the tumor volume following treatment with TLR7 agonist and anti-PD1 as determined by MRI imaging. Mice were treated with intravesical TLR7 agonist formulation (Vesimune) or Vehicle, followed by intravesical antibody (Isotype or anti-PD1) in RTGel (FIG. 4A) or in solution (FIG. 4B) or via the IP route (FIG. 4C). Fifteen (15) mice were treated from each group. MRI was performed on days 20-21 following tumor cells implantation.

Figures 5A, 5B, 5C:
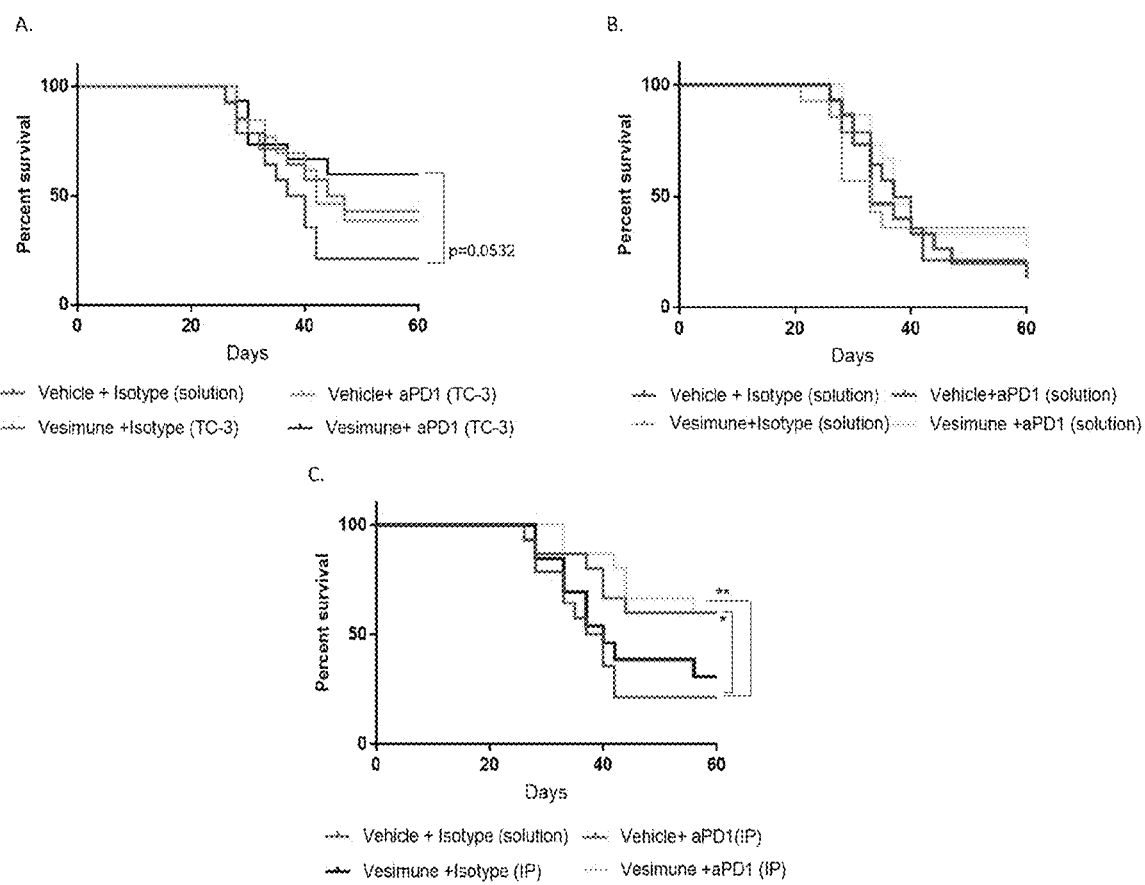

FIGS. 5A-5C show survival analysis of mice treated with intravesical TLR7 agonist formulation and anti-PD1. Mice were treated with intravesical TLR7 agonist formulation (Vesimune) or Vehicle, followed by intravesical antibody (Isotype or anti-PD1) in RTGel (FIG. 5A) or in solution (FIG. 5B) or via the IP route (FIG. 5C). Survival of the mice was monitored for a period of 60 days. Fifteen (15) mice were followed from each treatment group. *p<0.05 vs. control (vehicle+isotype), **p<0.005 vs. control (vehicle+isotype).

Figures 6A, 6B:
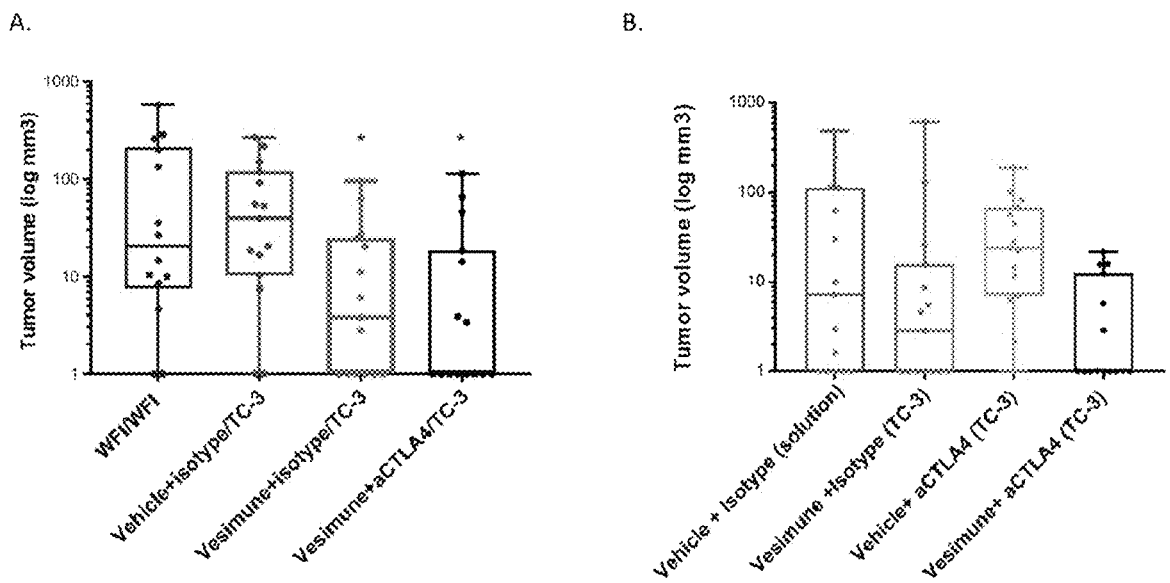

FIGS. 6A-6B show the tumor volume following treatment with TLR7 agonist and anti-CTLA4 as determined by MRI imaging. Mice were treated with intravesical TLR7 agonist formulation (Vesimune) or Vehicle, followed by intravesical antibody (Isotype or anti-CTLA4) in RTGel. Fifteen (15) mice were treated from each group. Additional control of WFI is included. MRI was performed on days 18-19 following tumor cells implantation (first study FIG. 6A). MRI was performed on days 20-21 following tumor cells implantation (second study FIG. 6B). *p<0.05 vs. control (vehicle+isotype).

Figures 7A, 7B:
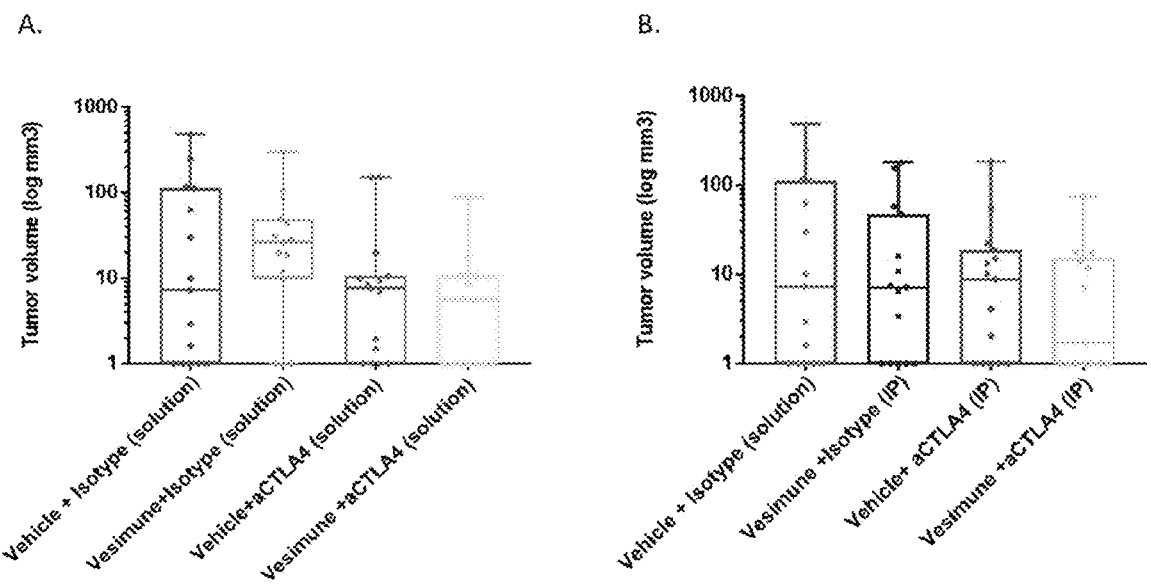

FIGS. 7A-7B show the tumor volume following treatment with TLR7 agonist and anti-CTLA4 as determined by MRI imaging. Mice were treated with intravesical TLR7 agonist formulation (Vesimune) or Vehicle, followed by intravesical antibody (Isotype or anti-CTLA4) in solution (FIG. 7A) or via the IP route (FIG. 7B). Fifteen (15) mice were treated from each group. MRI was performed on days 20-21 following tumor cells implantation.

Figures 8A, 8B, 8C:
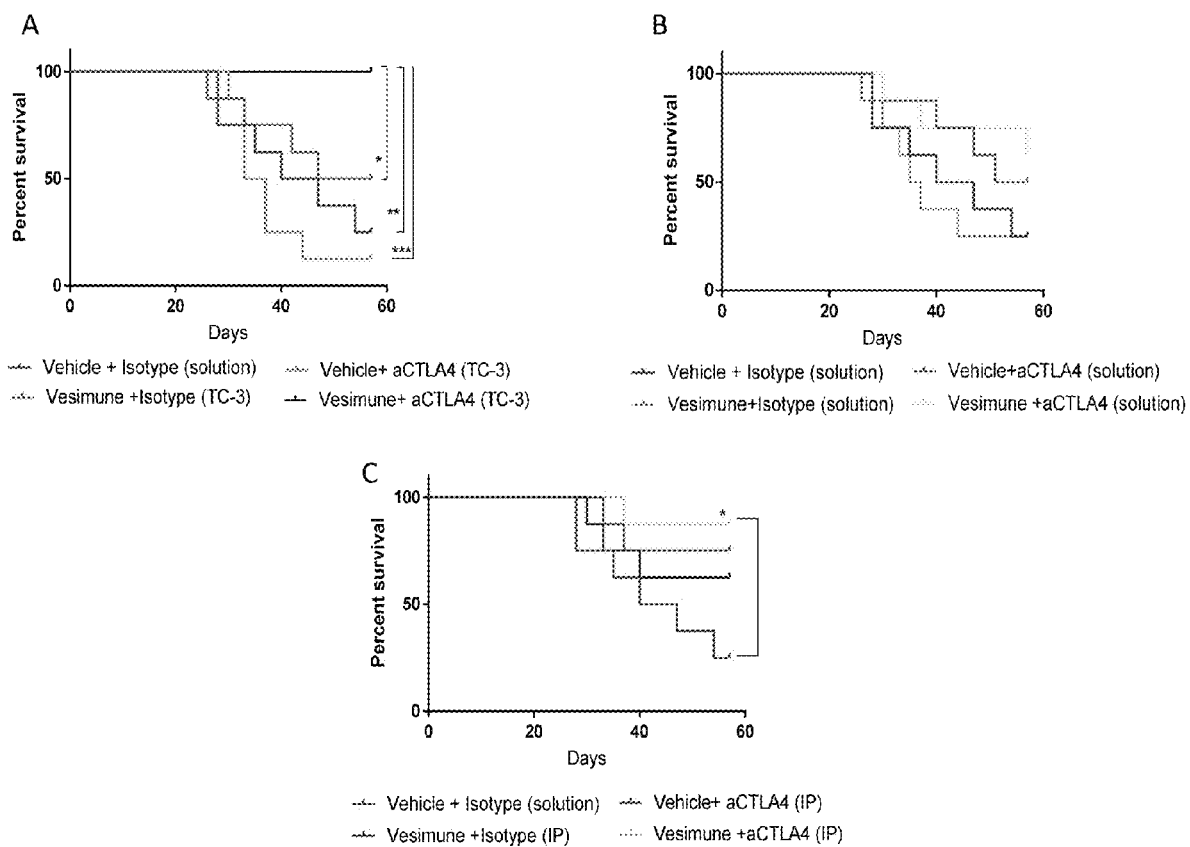

FIGS. 8A-8C show survival analysis of mice treated with TLR7 agonist formulation (Vesimune) and anti-CTLA4. Mice were treated with intravesical TLR7 agonist formulation or Vehicle, followed by intravesical antibody (Isotype or anti-CTLA4) in RTGel (FIG. 8A), or in solution (FIG. 8B), or via the IP route (FIG. 8C). Survival percentages of each group was monitored for a period of 60 days. *p<0.05 vs. control (vehicle+isotype), p<0.005 vs. control (vehicle+isotype), *p<0.0005 vs. control (vehicle+isotype).

Figures 9A, 9B, 9C:
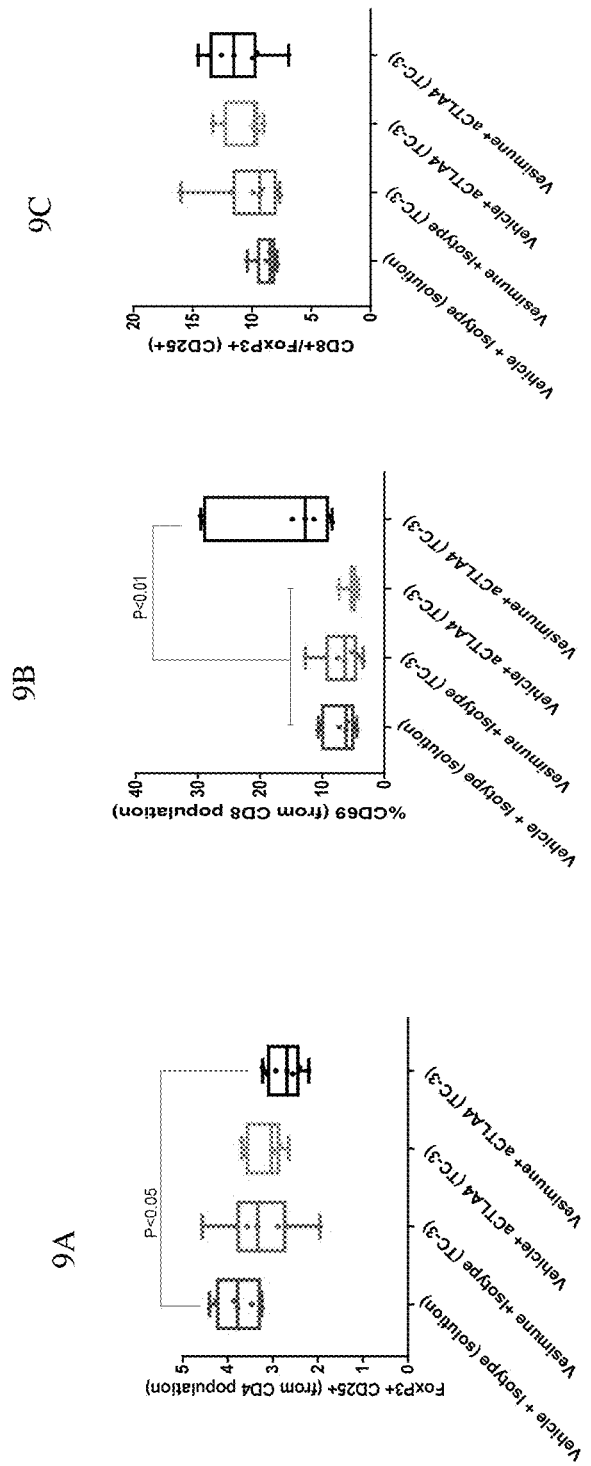

FIGS. 9A-9C show changes in major T cell populations in mice treated with intravesical TLR7 agonist formulation (Vesimune) and anti-CTLA4 in RTGel. Regional lymph nodes from 7 mice from each treatment group were harvested on day 23 following cell inoculation. Characterization and quantification of major T cell populations was done using FACS analysis. Percentage of the T regulatory cell population from the CD4+ population (CD4+CD25+FoxP3+) are shown (FIG. 9A). In addition, percentage of activated T effectors cells from the CD8+ population (CD8+CD69+) are shown (FIG. 9B) and the ratio between CD8+ expression (representing the T effector cells population) to FoxP3+CD25+ expression (representing the T regulatory cell population) is presented (FIG. 9C).

Figure 10:
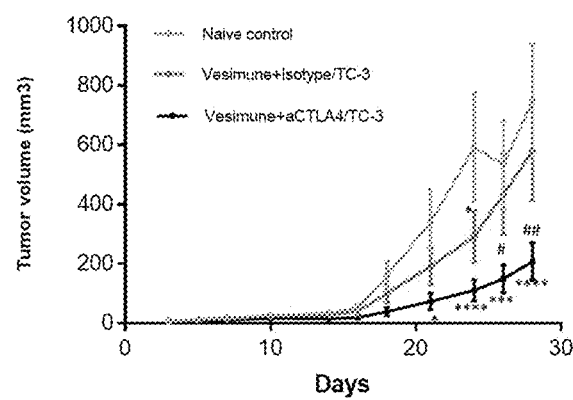

FIG. 10 shows the tumor volume following re-challenge with tumor cells. Mice that have recovered from the original tumor implantation (6 mice treated with intravesical TLR7 agonist formulation (Vesimune) and 10 mice treated with intravesical TLR7 agonist formulation and anti-CTLA4 in RTGel), as well as naïve mice (10 mice), were re-challenged by subcutaneous implantation of $1 \times 10^{\wedge}$MBT2 cells into the right flank. Day 0 is defined as the day of the subcutaneous tumor induction. Tumor volume was evaluated 3 times a week, up to day 28 following the re-challenge. *p<0.05 vs. naïve mice, *p<0.0005 vs. naïve mice, **p<0.0001 vs. naïve mice, # p<0.05 vs. intravesical TLR7 agonist formulation, ## p<0.005 vs intravesical TLR7 agonist formulation.

DETAILED DESCRIPTION

Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids, polypeptides, and small molecules are approximate, and are provided for description. Although methods and materials similar or equivalent to those described herein can be used in the practice or testing of this disclosure, suitable methods and materials are described below. The term "comprises" means "includes." "Consisting essentially of" indicates a composition, method, or process that includes only those listed features as the active or essential elements, but can include non-active elements in addition. The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Administration: The introduction of a composition into a subject by a chosen route. Administration of an active compound or composition can be by any route known to one of skill in the art, and as appropriate for the compound and the delivery system. For example, the compositions for use in the described methods are typically administered locally to the inside surface of a body cavity, such as by intravesical instillation (an exemplary form of local administration).

Analog, derivative or mimetic: An analog is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogs are often found using quantitative structure activity relationships (QSAR), with techniques such as those disclosed in Remington (*The Science and Practice of Pharmacology*, 19th Edition (1995), chapter 28). A derivative is a biologically active molecule derived from the base structure, and includes the "functional derivatives" described herein. A mimetic is a molecule that mimics the activity of another molecule, such as a biologically active molecule. Biologically active molecules can include chemical structures that mimic the biological activities of a compound. It is acknowledged that these terms may overlap in some circumstances. In particular embodiments of the claimed methods, analogs, derivatives, or mimetics having comparable activity to the expressly recited compounds can be used in place of the recited compounds.

Animal: Living multi-cellular vertebrate organisms, a category that includes for example, mammals and birds. The term mammal includes both human and non-human mammals. Similarly, the term subject includes both human and veterinary subjects, for example, humans, non-human primates, dogs, cats, horses, and cows. The term "primate" includes both human and non-human primates. "Non-human primates" are simian primates such as monkeys, chimpanzees, orangutans, baboons, and macaques. Similarly, the term "subject" includes both human and veterinary subjects, such as non-human primates, which have internal body cavities for which the described methods can be of benefit.

Antagonist: A molecule or compound that tends to nullify the action of another, or in some instances that blocks the ability of a given chemical to bind to its receptor or other interacting molecule, preventing a biological response. Antagonists are not limited to a specific type of compound, and may include in various embodiments peptides, antibodies and fragments thereof, and other organic or inorganic compounds (for example, peptidomimetics and small molecules). In a particular embodiment, an antagonist compound is one type of modulating compound.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one light (about 25 kD) and one heavy chain (about 50-70 kD). The N-terminus of each chain defines a variable region of about 100 to 110 or more amino acids primarily responsible for antigen recognition. The terms variable light chain ($V_L$) and variable heavy chain ($V_H$) refer, respectively, to these light and heavy chains.

As used herein, the term antibody includes intact immunoglobulins as well as a number of well-characterized fragments produced by digestion with various peptidases, or genetically engineered artificial antibodies. Thus, for example, pepsin digests an antibody below the disulfide linkages in the hinge region to produce F(ab)'$_2$, a dimer of Fab which itself is a light chain joined to $V_H$-$C_H$ 1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially a Fab with part of the hinge region (see, *Fundamental Immunology*, W. E. Paul, ed., Raven Press, N.Y., 1993). While various antibody fragments are defined in terms of the digestion of an intact antibody, it will be appreciated that Fab' fragments may be synthesized de novo either chemically or by utilizing recombinant DNA methodology. Thus, the term antibody as used herein also includes antibody fragments either produced by the modification of whole antibodies or synthesized de novo using recombinant DNA methodologies.

Antibodies for use in the methods, compositions, and systems of this disclosure can be monoclonal or polyclonal. Merely by way of example, monoclonal antibodies can be prepared from murine hybridomas according to the classical method of Kohler and Milstein (*Nature* 256:495-497, 1975) or derivative methods thereof. Detailed procedures for monoclonal antibody production are described in Harlow and Lane (*Antibodies, A Laboratory Manual*, CSHL, New York, 1988).

The terms bind specifically and specific binding refer to the ability of a specific binding agent (such as, an antibody) to bind to a target molecular species in preference to binding to other molecular species with which the specific binding agent and target molecular species are admixed. A specific binding agent is said specifically to recognize a target molecular species when it can bind specifically to that target.

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science*, 242:423-426, 1988; Huston et al., *Proc. Natl. Acad. Sci.*, 85:5879-5883, 1988). Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.*, 90:6444-6448, 1993; Poljak et al., *Structure*, 2:1121-1123, 1994). One or more CDRs may be incorporated into a molecule either covalently or noncovalently to make the resultant molecule an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest. A chimeric antibody is an antibody that contains one or more regions from one antibody and one or more regions from one or more other antibodies.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

A neutralizing antibody or an inhibitory antibody is an antibody that inhibits at least one activity of a target—usually a polypeptide—such as by blocking the binding of the polypeptide to a ligand to which it normally binds, or by disrupting or otherwise interfering with a protein-protein interaction of the polypeptide with a second polypeptide. An activating antibody is an antibody that increases an activity of a polypeptide. Antibodies may function as mimics of a target protein activity, or as blockers of the target protein activity, with therapeutic effect derived therein.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Body cavity: Any fluid-filled space internal to a multicellular organism. In particular embodiments, a body cavity can include other body cavities. For example, the mammalian pelvic cavity includes the bladder, and the thoracic cavity includes the upper gastro-intestinal tract and cavities such as the esophagus. In particular embodiments, a body cavity can be the urinary tract, such as the bladder and/or the pyelocaliceal system and/or the ureters.

Cancer: A malignant disease characterized by the abnormal growth and differentiation of cells. The product of neoplasia is a neoplasm (a tumor or cancer), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder. A "cancer cell" is a cell that is neoplastic, for example a cell or cell line isolated from a tumor.

Examples of solid tumors, such as sarcomas and carcinomas, and which include cancers of internal body cavities, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers (such as small cell lung carcinoma and non-small cell lung carcinoma), ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma, astrocytoma, medulloblastoma, craniopharyogioma, ependymoma, pinealoma, hemangioblastoma, acoustic neuroma, oligodendroglioma, menangioma, neuroblastoma and retinoblastoma).

Chemotherapeutic agent: An agent with therapeutic usefulness in the treatment of diseases characterized by abnormal cell growth or hyperplasia. Such diseases include cancer, autoimmune disease as well as diseases characterized by hyperplastic growth such as psoriasis. In one embodiment, a chemotherapeutic agent is a radioactive compound. One of skill in the art can readily identify a chemotherapeutic agent (for instance, see Slapak and Kufe, *Principles of Cancer Therapy*, Chapter 86 in *Harrison's Principles of Internal Medicine*, 14th edition; Perry et al., *Chemotherapy*, Ch. 17 in Abeloff, *Clinical Oncology* $2^{nd}$ ed., © 2000 Churchill Livingstone, Inc.; Baltzer L, Berkery R (eds): *Oncology Pocket Guide to Chemotherapy*, 2nd ed. St. Louis, Mosby-Year Book, 1995; Fischer D S, Knobf M F, Durivage H J (eds): *The Cancer Chemotherapy Handbook*, 4th ed. St. Louis, Mosby-Year Book, 1993). Chemotherapeutic agents include small molecule agents and biologic agents. The chemotherapeutic agent can be administered before, concurrently, or subsequent to the described methods for treatment of the cancer with the TLR agonist, immune checkpoint modulator and thermo-reversible hydrogel composition.

Effective amount of a compound: A quantity of compound sufficient to achieve a desired effect in a subject being treated. An effective amount or "therapeutically effective amount" of a compound can be administered in a single dose, or in several doses, for example daily, during a course of treatment. However, the effective amount of the compound will be dependent on the compound applied, the subject being treated, the severity and type of the affliction, and the manner of administration of the compound. In a particular example, an effective amount of the active agents in the described compositions and treatments, namely the at least one TLR agonist and at least one immune check point modulator (i.e. inhibitor or inducing agent) is an amount that provides to a human subject receiving the composition, an anti-cancer effect that is greater than the effect that would be produced upon treatment with either agent alone, and which in particular embodiments is a synergistic effect.

Intravesical instillation: Also known as "intravesical therapy;" a medical procedure involving the direct/local administration of a drug into the bladder. Comparable drug administration is possible for other body cavities. In particular embodiments, intravesical instillation involves delivery of a drug through a catheter. In particular embodiments of the methods described herein, hydrogel-based compositions, such as reverse thermal (thermoreversible) hydrogels are provided to a subject by intravesical instillation.

Inhibiting protein activity: To decrease, limit, or block an action, function or expression of a protein. The phrase inhibit protein activity is not intended to be an absolute term. Instead, the phrase is intended to convey a wide-range of inhibitory effects that various agents may have on the normal (for example, uninhibited or control) protein activity. Inhibition of protein activity may, but need not, result in an increase in the level or activity of an indicator of the protein's activity. By way of example, this can happen when the protein of interest is acting as an inhibitor or suppressor of a downstream indicator. Thus, protein activity may be inhibited when the level or activity of any direct or indirect indicator of the protein's activity is changed (for example, increased or decreased) by at least 10%, at least 20%, at least 30%, at least 50%, at least 80%, at least 100% or at least 250% or more as compared to control measurements of the same indicator.

Immunotherapy: A method of evoking an immune response against on their production of target antigens. Immunotherapy based on cell-mediated immune responses involves generating a cell-mediated response to cells that produce particular antigenic determinants, while immunotherapy based on humoral immune responses involves generating specific antibodies to virus that produce particular antigenic determinants.

Modulator: a compound or composition that regulates or changes the activity of a molecule or a biochemical pathway, either by its inhibiting or inducing its activity. Non-limiting examples of such modulators are small molecule antagonists, small molecule agonists or antibodies, as a form of peptide modulators, and which can be agonists or antagonists.

Pharmaceutically acceptable carriers: The active agents for use in the described methods can be, mixed with a pharmaceutically acceptable carrier. The pharmaceutically acceptable carriers useful in this disclosure are conventional. *Remington's Pharmaceutical Sciences*, by E. W. Martin, Mack Publishing Co., Easton, Pa., 15th Edition (1975), and updates thereof, describes compositions and formulations suitable for pharmaceutical delivery of the compounds herein disclosed.

Pharmaceutical agent: A chemical compound or composition capable of inducing a desired therapeutic or prophylactic effect when properly administered to a subject or a cell. Incubating includes exposing a target to an agent for a sufficient period of time for the agent to interact with a cell. Contacting includes incubating an agent in solid or in liquid form with a cell.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), and updates thereof, describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing or treating a disease: Preventing a disease refers to inhibiting the full development of a disease, for example inhibiting the development of myocardial infarction in a person who has coronary artery disease or inhibiting the progression or metastasis of a tumor in a subject with a neoplasm. Treatment refers to a therapeutic intervention that ameliorates a sign or symptom of a disease or pathological condition after it has begun to develop. Preventing and treating a disease can also refer to the results of interventions taken to prevent the recurrence of a disease that has been otherwise treated, such as surgery to remove a solid tumor in an internal body cavity.

Radiation Therapy (Radiotherapy): The treatment of disease (e.g., cancer or another hyperproliferative disease or condition) by exposure of a subject or their tissue to a radioactive substance. Radiation therapy is the medical use of ionizing radiation as part of cancer treatment to control malignant cells. Radiotherapy may be used for curative or adjuvant cancer treatment. It is used as palliative treatment where cure is not possible and the aim is for local disease control or symptomatic relief. The radiotherapy can be administered before, concurrently, or subsequent to the described methods for treatment of the cancer with the TLR agonist, immune checkpoint modulator and thermoreversible hydrogel composition.

Subject susceptible to a disease or condition: A subject capable of, prone to, or predisposed to developing (or redeveloping) a disease or condition. It is understood that a subject already having or showing symptoms of a disease or condition is considered "susceptible" since they have already developed it.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound. For example, a therapeutically effective amount of an active ingredient can be measured as the concentration (moles per liter or molar-M) of the active ingredient (such as a small molecule, peptide, protein, or antibody) in blood (in vivo) or a buffer (in vitro) that produces an effect.

Thermoreversible hydrogel: The thermoreversible hydrogels for use in the described methods are in liquid form at low temperatures and remain liquid in the process of administration to a patient (e.g. through intravesical instillation). At elevated temperatures (e.g. typical human body temperature), thermoreversible hydrogel solidifies, such as in a coating of an internal body cavity. Low temperature can be defined less than 20° C., preferably less than 15° C. In particular embodiment this low temperature can be less than 10° C. As used herein, a thermoreversible hydrogel is synonymous with a "reverse thermal hydrogel" and a "thermo-reversible hydrogel." Particular examples of a thermoreversible hydrogel include compositions such as RTgel, which include a poloxamer with additional optional ingredients including HPMC.

Urinary tract cancer: Cancer of any area of the urinary tract, including the urothelium, kidney, ureter, bladder (also referred to as "urinary bladder"), lamina propria, bladder muscle and urethra. As defined by the T0, Ta, T1, T2, T3 and T4. Surgery followed by intravesical instillation of chemotherapy is a common treatment for urinary tract solid tumors. Treatment may also include systemic chemotherapy and radiation for advanced types of urinary cancer.

Wash: Use of a fluid to cleanse an area. In particular embodiments, the "wash" of an area results in complete cleansing of the area. In other embodiments, washing an area does not produce complete cleansing. In particular embodiments of the described methods, a body cavity is "washed" between application of compositions containing a hydrogel and a therapeutic agent. In particular embodiments, the composition is completely washed out of the body cavity. In other embodiments, the composition is not completely washed out of the body cavity. The wash (and removal of fluid) of the methods described herein can be accomplished by standard methods of introducing and removing fluid from a body cavity.

Overview of Several Embodiments

Described herein is method of treatment for a cancer of an internal body cavity in a human subject, which includes administering to a subject in need thereof a therapeutically effective amount of a TLR agonist, and an immune checkpoint modulator, such as an immune checkpoint inhibitor or inducer, wherein at least one of the TLR agonist and the immune checkpoint modulator are provided in a thermoreversible hydrogel composition comprising chitosan or at least one tri block copolymer having a general formula ABA or BAB copolymer, wherein A is a hydrophilic block and B is a hydrophobic block, thereby treating the cancer of the body cavity.

In particular embodiments the TLR agonist is a TLR-2, TLR-4, TLR-7, TLR7/8, TLR-8, or TLR-9 agonist.

In further embodiments the TLR agonist includes an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, TMX101, MEDI9197, TMX 201, TMX 202, TMX-30X, TMX302, NKTR-262, Motolimod, DUK-CPG-001, AST-008, IMO-2125, CMP-001, IMO-2055 (EMD1201081), CpG-28, agatolimod, SD-101, MGN1703, G100, BCG, QS-21, or AS15.

In particular embodiments the immune checkpoint modulator can be an inhibitor that is anti-PD1, anti-PDL1, anti-CTLA4, anti-KIR, anti-LAG3, anti-VISTA, anti-TIM3, anti-B7-H3, anti-B7-H4, and anti-BTLA.

In particular embodiments the immune checkpoint modulator is an antagonistic antibody for example: Pembrolizumab (Keytrude, MK-3475), Cemiplimab (AGEN-2034), Nivolumab (Opdivo,BMS-936558), Pidilizumab (CT-011), MEDI0680 (AMP514), TSR-042, AMP-224, Durvalumab (MEDI4736), Avelumab (MSB0010718C), Atezolizumab (MPDL3280A), CK-301, MDX1105 (BMS-936559), Ipilimumab (Yervoy), Tremelimumab (CP-675,206), Lirlumab (BMS986015), IPH2101, Relatlimab (BMS986016), IMP321, TSR-033, JNJ-61610588, CA-170, BMS-986207, TSR022, Enoblituzumab (MGA271), MGD009, AGEN-1884, AGEN-2041 (AGEN-1181), ADU-1604, AK 104, ALPN-202, BCD-145, BMS-986249, BPI-002, CBT-509, ADU-1604, ATOR 1144, ATOR-1015, and DS-5573a.

In additional embodiments the immune checkpoint modulator is an agonist antibody that binds to an antigen such as 41BB (CD137), OX40 (CD134), CD28, ICOS (CD278) or CD40. In further embodiments the antibody may be Utomilumab (PF05082566), Urelumab (BMS663516), MEDI6469, PF04518600 (PF-8600), MOXRO916, AMG228, GSK3174998, TGN1412 (TAB08), MEDI-570, GSK3359609, CP870890 and APX005M.

In particular embodiments the tri block copolymer has an ABA formula of EPO/PPO/EPO block copolymer. In other embodiments the tri block copolymer has an ABA formula with an average molecular weight of 8500-16000 DA, inclusive.

In some embodiments the tri block copolymer has an ABA formula of Poloxamer. In particular embodiments the Poloxamer is Poloxamer 407, Poloxamer 188, Poloxamer 124, Poloxamer 237, and Poloxamer 338. In a particular embodiment the Poloxamer is Poloxamer 407.

In some embodiments the cancer includes bladder cancer, urinary tract cancer, upper urinary tract cancer, renal cancer, gastrointestinal cancer, colon cancer, rectal cancer, and female reproductive system cancer. Other examples of cancers treated with the described methods can be upper tract urothelial carcinoma (UTUC), non-muscle invasive bladder cancer (NMIBC), muscle invasive bladder cancer (MIBC), or metastatic bladder cancer.

In some embodiments the thermoreversible hydrogel composition also includes 0.1% (w/w) to 5% (w/w) mucoadhesive polymer. In particular embodiments the thermoreversible hydrogel composition includes 15% (w/w)-40% (w/w) poloxamer 407.

In other embodiments the TLR-7 agonist is an imidazoquinolin (amine) derivative provided at a concentration of 0.005% (w/v) to 10% (w/v).

In particular embodiments, the immune checkpoint modulator is an antibody that is provided at a concentration of 0.5 (mg/Kg B·W) to 100 (mg/Kg B·W).

In other embodiments the immune checkpoint modulator is an CTLA4 inhibitor that is Ipilimumab or Tremelimuab provided at a concentration 1 (mg/Kg B·W) to 50 (mg/Kg B·W). In other embodiments it is a PDL-1 inhibitor that is Atezolizumab, Durvalumab, or Avelumab provided at a concentration of 5 (mg/Kg B·W) to 70 (mg/Kg B·W). In still other embodiments it is a PD-1 inhibitor that is Pembrolizumab or Nivolumab provided at a concentration of 0.5 (mg/Kg B·W) to 50 (mg/Kg B·W).

In some embodiments the TLR agonist is administered locally, such as by intravesical instillation. In other embodiments the immune checkpoint modulator is administered systemically or locally.

In particular embodiments the TLR agonist and the immune checkpoint modulator are provided in the thermoreversible hydrogel locally into the internal body cavity, such as by intravesical instillation. In other embodiments the TLR agonist and immune checkpoint modulator are administered simultaneously, repetitively, in sequence or in any combination thereof.

Additional methods described herein are methods for inhibiting re-growth of a cancer of an internal body cavity in a human subject, the method which includes administering to a subject in need thereof a therapeutically effective amount of: a TLR agonist, and an immune checkpoint modulator, wherein at least one of the TLR agonist and the immune checkpoint modulator are provided in a thermoreversible hydrogel composition including chitosan or at least one tri block copolymer having a general formula ABA or BAB copolymer, wherein A is a hydrophilic block and B is a hydrophobic block, and wherein the TLR agonist and immune checkpoint modulator are administered to the subject subsequent to a treatment for the cancer which removed or decreased the amount of the cancer in the subject, thereby inhibiting the regrowth cancer of the body cavity.

Further methods described herein are methods for treating a cancer of an internal body cavity in a subject, including administering to a subject in need thereof (a) a therapeutically effective amount of a TLR agonist, and (b) a therapeutically effective amount of an immune checkpoint modulator selected from the group consisting of anti-PD1, anti-PDL1, and anti-CTLA4; wherein (a) and (b) are provided separately in a thermo-reversible hydrogel composition comprising a chitosan or tri block copolymer having a general formula ABA or BAB, wherein A is a hydrophilic block and B is a hydrophobic block, and administered locally into the internal body cavity.

Additionally described herein are compositions including a TLR agonist, and an immune checkpoint modulator, such as an immune checkpoint inhibitor, wherein at least one of the TLR agonist and the immune checkpoint modulator are formulated in a thermo-reversible hydrogel composition comprising chitosan or at least one tri block copolymer having a general formula ABA or BAB copolymer, wherein A is a hydrophilic block and B is a hydrophobic block.

In some embodiments the TLR agonist of the composition can be TLR-2, TLR-4, TLR-7, TLR-7/8, TLR-8, and TLR-9 agonist.

In some embodiments the immune checkpoint modulator of the composition can be an inhibitor that is anti-PD1, anti-PDL1, and anti-CTLA4.

Combination Immunomodulatory Treatment—

Described herein are compositions for treating a cancer found in or on the surface of an internal body cavity, such as a cavity of the urinary tract. The described compositions include combinations of (a) a Toll-Like Receptor (TLR) agonist, (b) a modulator (inhibitor or agonist) of an immune check point peptide such as but not limited to CTLA-4, PDL-1 or PD-1, wherein at least one of the TLR agonist and the immune checkpoint modulator are provided in the thermo-reversible hydrogel, Toll-like receptor agonists used as single agents especially when applied locally can effectively eradicate tumors due to their potent stimulation of innate and adaptive immunity as well as their effects on the tumor microenvironment. Two TLR agonists, bacillus Calmette-Guerin (BCG) and imiquimod are US FDA approved for clinical use as monotherapy for cancer.

The TLR agonist of the described compositions can be any agent capable of stimulating one or more members of the TLR family (such as TLR-7, TLR-8, TLR-9, TLR-2, TLR-4, TLR-7/8 and the like) with resultant stimulating effects on innate and adaptive immune response, such as on dendritic cells, B cells, T cells, mast cells, and NK (natural killer)/NKT cells. TLR stimulation is also associated with the induction of tumor cell apoptosis. TLRs can be expressed on normal human urothelium cells enabling possible stimulation by TLR agonists.

In particular embodiments, the TLR agonist is a peptide, antibody, or small molecule, or functional derivative thereof. In specific non-limiting embodiments, the TLR agonist is the TLR-7 agonist. One non limiting example of a TLR-7 agonist is imiquimod, as shown below or resiquimod

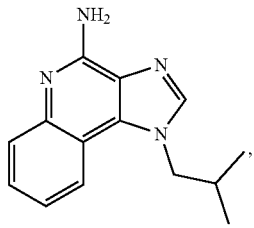 [SMILES: CC(C)Cn1cnc2c(N)nc3ccccc3c21]

including any derivatives of imiquimod/resiquimod, or synthetic molecules or conjugates, which can include modifications in chemical structure, which retaining the ability to act as a TLR-7 agonist. Such derivatives are often described as a "functional derivative". In specific non-limiting embodiments, the TLR7/8 agonist is formulated as TMX101 (TMX101 is a formulation of imiquimod for intravesical instillation, also referred to herein as vesimune). In specific non-limiting embodiments, the TLR agonist is a TLR-7/8 agonist. One non-limiting example of a TLR-7/8 agonist is NKTR-262. In specific non-limiting embodiments, the TLR agonist is a TLR-9 agonist. Some non-limiting examples of TLR-9 agonists are AST-008, IMO-2125, and CMP-001. In particular embodiments, the TLR agonist for use in the described compositions and methods include an imidazoquinoline amine (Imiquimod (R837) (InvivoGen, San Diego Calif.)), tetrahydroimidazoquinoline amine (see: WO 2007079169), imidazopyridine amine (see: WO 2001074343), 1,2-bridged imidazoquinoline amine (see: WO 2007079169), 6,7-fused cycloalkylimidazopyridine amine (see: U.S. Pat. No. 6,894,060), imidazonaphthyridine amine (see: WO 2008036312), tetrahydroimidazonaphthyridine amine (see: U.S. Pat. No. 6,894,060), oxazoloquinoline amine (see: U.S. Pat. No. 6,894,060), thiazoloquinoline amine (see: WO 2005055932), oxazolopyridine amine (see: CA 2475595), thiazolopyridine amine, (see: CA 2475595), oxazolonaphthyridine amine (see: CA 2475595), thiazolonaphthyridine amine, (see: CA 2475595), TMX 101 (Vesimune), TMX 201, TMX 202, TMX-30X, TMX302 (see: WO 2016044182), CpG-283, agatolimod4, QS-21, Motolimod ((VTX-2337) APExBIO, Boston Mass.)), BCG, AS15; and DUK-CPG-001, IMO-2055 (EMD1201081), SD-101, MGN1703, and G100 (GLA-SE) (which can be found in the National Cancer Institute Drug Dictionary (available online at cancer.gov/publications/dictionaries/cancer-drug). In a particular embodiment, the TLR-7 agonist is imidazoquinolin (amine) derivative provided in an amount of 0.005% (w/v) to 10% (w/v), including an amount of 0.01% (w/v) to 5% (w/v), an amount of 0.1% (w/v) to 4% (w/v), an amount of 0.1% (w/v) to 3% (w/v), an amount of 0.1% (w/v) to 2% (w/v), with the preferred concentration of 0.4%.

According to another preferred embodiment of the present invention, the TLR-7 agonist is embedded in a pharmaceutical composition further that comprises at least one polymer, wherein this polymer is preferably selected from chitosan or its derivatives, or from a poly(ethylene oxide)-poly(propylene oxide)-poly(ethylene oxide) copolymer (also termed PEO-PPO-PEO or poloxamer). In other embodiments, the composition further includes an organic acid, such as but not limited to lactic acid, citric acid, or acetic acid.

Antagonists of CTLA-4, PDL-1 and PD-1 for use in the described composition include any agent capable of binding to CTLA-4, PDL-1, or PD-1 and which can prevent binding to their ligands, such as presented by a tumor cell, antigen presenting cells or other immune cells. In particular embodiments, the antagonists include blocking peptides, antibodies or small molecules or combination thereof.

In particular embodiments, the immune checkpoint modulator is an antagonist antibody selected from anti-PD1, anti-PDL1, anti-CTLA4, anti-KIR, anti-LAG3, anti-VISTA, anti-TIM3, anti-B7-H3, anti-B7-H4, and anti-BTLA.

In other particular embodiments, the immune checkpoint modulator is an agonist antibody that binds to an antigen selected from 41BB (CD137), OX40 (CD134), CD28, ICOS (CD278) or CD40.

The checkpoint modulator can be an antagonistic antibody comprising Pembrolizumab (Keytrude, MK-3475), Cemiplimab (AGEN-2034), Nivolumab (Opdivo,BMS-936558), Pidilizumab (CT-011), MEDI0680 (AMP514), TSR-042, AMP-224, Durvalumab (MEDI4736), Avelumab (MSB0010718C), Atezolizumab (MPDL3280A), MDX1105 (BMS-936559), Ipilimumab (Yervoy), Tremelimumab (CP-675,206), Lirlumab (BMS986015), IPH2101, Relatlimab (BMS986016), IMP321, TSR-033, JNJ-61610588, CA-170, BMS-986207, TSR022, Enoblituzumab (MGA271), MGD009, AGEN-1884, AGEN-2041 (AGEN-1181), ADU-1604, AK 104, ALPN-202, BCD-145, BMS-986249, BPI-002, CBT-509, ADU-1604, ATOR 1144, ATOR-1015, DS-5573a, or any combination thereof.

In some embodiments, the check point modulator is an antibody comprising Pembrolizumab, Ipilimumab, Tremelimumab, Atezolizumab or Durvalumab or Avelumab.

The thermoreversible hydrogel composition of the described compositions includes a tri block copolymer having a general formulae ABA or BAB copolymer, wherein A is a hydrophilic block and B is a hydrophobic block. More specifically, A or B is selected from PEO ((Poly(ethylene oxide)), PLGA (poly(lactic-co-glycolic) acid, PLA (polylactic acid) and PPO (polypropylene oxide) PGA (Poly Glycolic Acid), PCL—(Polycaprolactonn), PCLA-Poly (ε-caprolactone-co-lactide), PCBCL-poly (α-carboxylate-co-α-benzylcarboxylate-ε-caprolactone), or includes at least two cyclic monomers selected from the group consisting of glycolide, lactide, ε-caprolactone, p-dioxanone (1,4-dioxan-2-one), trimethylene carbonate (1,3-dioxan-2-one); 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; chi-diethylpropiolactone; ethylene carbonate; ethylene oxalate; 3-methyl-1,4-dioxane-2,5 dione; 3,3-diethyl-1,4-dioxan-2,5-dione, 6,8 dioxabicycloctane-7-one; beta-propiolactone; gama-butyrolactone,delta-valerolactone; epsilon-decalactone, 3-methyl-1,4-dioxane-2,5dione; 1,4-dioxane-2,5-dione; 2,5-diketomorpholine, alpha,alpha-diethylpropiolactone, gama-butyrolactone; 1,4-dioxepan-2-one, 1,5-dioxepan-2-one; 6,6-dimethyl-dioxepan-2-one; 6,6-dioxabicycloctane-7-one; or 5, 5-dimethyl-1,3-dioxan-2-one.

In some embodiments the described hydrogel is RTGel, a thermoreversible hydrogel composed of Poloxamer, with an optional component such a hydroxypropyl methylcellulose (HPMC).

In particular embodiment the thermoreversible hydrogel composition includes a tri block copolymer having a formula of PEO/PPO/PEO and has an average molecular weight in the range of 8500-16000 DA.

In particular embodiments, the thermoreversible hydrogel composition includes a poloxamer or combination of different poloxamers such as but not limited to Poloxamer 407, Poloxamer 108, and Poloxamer 68.

In particular embodiments the gel component of the thermoreversible hydrogel compositions is present in concentrations of 5%-45% (w/w) and ranges therein, such as 10%-35%, 20%-45%, 15%-35%, 20%-40%, 20%-35%. In another particular embodiment, the gel component is present in a concentration of 24% or 32%.

In a particular embodiment, the thermoreversible hydrogel composition includes 5% to 45% (w/w), and any range therein, of a PEO/PPO block copolymer and also includes at least one of a mucoadhesive enhancing agents, dissolution rate controlling agent, gelation temperature controlling agent, pH controlling agent, absorption enhancer/tight junction modifier/cell membrane permeability enhancer, organic acid or cyclodextrins.

In particular embodiments, the mucoadhesive enhancing agent can include, but is not limited to, HPMC (hydroxyl propylmethyl cellulose), agarose, chitosan, gelatin, hyaluronic acid, carrageenan, pectin, sodium alginate, polyacrylic acids, polymers based on poly(meth)acrylic acid, carbopol, polycarbophil, polyacrylic acid, polyacrylates, copolymer of acrylic acid and polyethylene glycol, copolymer of methylvinyl ether and methacrylic acid, poly-2-hydroxyethylmethacrylate, copolymer of acrylic acid and ethylhexylacrylate, cellulose derivatives (for example methylcellulose (MC), hydroxy-propylcellulose (HPC), hydroxy ethyl cellulose, thiolated CMC other hydroxyalkylcelluloses and hydroxyalkylmethylcelluloses, carboxy-methylcelluloses (CMC), Polyvinylpyrrolidone (PVP) and its copolymers (N-vinyl-2-pyrrolidone), Poly-N-2-hydroxypropylmethacrylamide, polyhydroxyethylene, polyvinyl alcohol (PVA), and thiolated polymers.

In particular embodiments, dissolution rate controlling agents can include, but are not limited, to silicon dioxide or any derivatives thereof, nanoparticles or microparticles of Poly (Lactide-co-Glycolide (PLGA), polylactic acid (PLA), Polyglycolic acid (PGA), PLA-PEG or PLGA-PEG copolymers, nanoparticles or microparticles polystyrene or polymethyl methacrylate (PMMA), calcium carbonate, microcrystalline cellulose, aluminum hydroxide, Eudragit® NE, Eudragit® RS and RL, cellulose acetate and cellulose acetate butyrate, crospovidones, crosslinked sodium carboxymethylcellulose, crosslinked sodium carboxymethylstarch, thickening agents, soy, iodinated aromatic compounds, cyclodextrin, and cholesterol.

In particular embodiments, gelation temperature controlling agents include, but are not limited to, urea, polyethylene glycol, short chain fatty acid and their salts (sodium octanoate, sodium dodecyl sulfate), ethanol, Glyceryl monostreatrate, Isopropyl myristate, and Polysorbate surfactants.

In some embodiments, tight junction modifier/cell membrane permeability enhancers include, but are not limited to, anionic surfactants, non-anionic surfactants, charged polymers, dimethyl sulfoxide (DMSO), decylmethyl sulfoxide, tert-butyl cyclohexanol, fatty acids their esters and salts, ethanol, nicotinamide, urea, perfluoropolyether, monoterpene ketones, disodium citrate, succinic acid, alkyl saccharides, hyaluronidase and tris.

In some embodiments pH modifying substances include: group consisting of acids, bases and buffer substances, adipic acid, malic acid, lactic acid, ascorbic acid, aspartic acid, benzenesulfonic acid, benzoic acid, succinic acid, citric acid, ethanesulfonic acid, 2-hydroxyethanesulfonic acid, fumaric acid, gluconic acid, glucuronic acid, glutamic acid, potassium hydrogentartrate, maleic acid, malonic acid, methanesulfonic acid, toluenesulfonic acid, trometamol, tartaric acid, Tris-HCl, NaOH, sodium caprylate phosphate buffer.

In another embodiment, the thermoreversible hydrogel includes between 10% and 45% (w/w) Poloxamer or mixture of different poloxamers and between 0.05% and 0.5% (w/w) mucoadhesive agent.

In other embodiments the thermoreversible hydrogel includes between 10% and 35% (w/w) EPO/PPO block copolymer and between 0.1% and 5% (w/w) mucoadhesive agent.

In particular embodiments, the pharmaceutical composition can be sterile. In other particular embodiments, the pharmaceutical composition can further include a pharmaceutically acceptable carrier, diluent, or salt, all of which are standard and known in the art.

Kits

It will be appreciated that in particular embodiments, the effective amounts of the described combination of TLR agonist and immune check point modulator (e.g. CTLA-4, PDL-1, or PD-1 antagonist) can be provided in a combined formulation with a desired thermoreversible hydrogel. Conversely, in particular embodiments, the agonist and antagonist components can be provided in separate thermoreversible hydrogel formulations having distinct properties and abilities to release the provided active agents over a period of time and under particular conditions.

Accordingly, kits are described herein that can provide the components of the described compositions in various forms and configurations as needed. In a particular embodiment such kits include the TLR agonist and, immune check point modulator along with a single specific thermoreversible hydrogel formulation, in either separate aliquots or combined in a single aliquot, that is either ready to administer (is in liquid form) or is lyophilized or otherwise desiccated and requires reconstitution in an aqueous solvent (such as water) prior to administration.

In other embodiments, the kits contain multiple thermoreversible hydrogel formulations, which biodegrade, and thereby release an incorporated active agent, at different rates. In particular examples, the components of such kits are ready to administer; in other examples, they are desiccated and need to be reconstituted. In certain examples, the active agents are provided separate from the hydrogel formulations. In other examples, the active agents pre-mixed with the desired hydrogel formulations.

It will be appreciated that all of the kits described herein can include instructions for preparing and administering the described combination treatments, in general and also with respect to the particular conditions that being treated.

Treatments for Cancers of Internal Body Cavities

Additionally, described herein are methods for treatment of a cancer of an internal body cavity by administration of a combination of an effective amount of a TLR agonist and an effective amount of an immune checkpoint modulator, wherein the at least one of the active agents are provided in a local, sustained manner, such as by intravesical instillation, by one or more thermoreversible hydrogel compositions.

In a particular embodiment, the body cavity is any internal body cavity that produces and/or voids fluid in such a way that locally administered liquid agents (or any other agent that is not able to adhere to the internal surface of the body cavity), such as by instillation (e.g. intravesical administration), are quickly flushed from the site of administration due to urine production and micturition. Particular non-limiting examples of such cavities include the bladder, the upper urinary tract (including: the ureters, renal pelvis and calyces), uterus, ovary, fallopian tube, cervix, pancreas, esophageal cavity, stomach cavity, intestinal cavity, and colon cavity, abdomen, and the gastrointestinal tract. Within this disclosure, body cavities for treatment with the described compositions and methods include organs adjacent to the indicated body cavities such as, but not limited to, a liver lobe.

In particular embodiments the cancer is a solid cancer found on or in the surface of an internal body cavity (e.g. the wall of the cavity in contact with the cavity space). Particular non limiting examples include bladder cancer, upper urinary tract cancer, gastrointestinal cancer, vaginal cancer, rectal cancer, thoracic cancer, and pelvic cancer. In other particular embodiments the cancer is refractory or develops resistance to standard chemotherapeutic treatment.

The methods described herein include administration of at least one of the described immunomodulatory agents in a thermoreversible hydrogel, such as the thermoreversible hydrogel compositions described herein. Accordingly, it will be appreciated that unlike traditional methods of administering active agents systemically or by instillation in a standard liquid formulation, the compositions can remain associated with the local area of administration for an extended period of time. In particular embodiments, such as when both a TLR agonist and immune checkpoint modulator are administered via a hydrogel polymer, the TLR agonist and immune checkpoint modulator, such as checkpoint antagonist, can remain in contact with the body cavity under treatment for the same amount of time. In such embodiments, the TLR agonist and immune checkpoint modulator can be provided in the same or different thermoreversible hydrogel compositions. In other embodiments, separate thermoreversible hydrogel compositions that include each of the active agents remain in contact with the body cavity for different prolonged times. The duration of treatment (and therefore of contact of each composition with the body cavity) in any of these embodiments can be hours or substantially longer, such as one or several days.

In particular embodiments, the composition or compositions can contact the body cavity for up to 72 hours, up to 36 hours, up to 24 hours, up to 22 hours, up to 20 hours, up to 18 hours, up to 16 hours, up to 14 hours, up to 12 hours, up to 10 hours, up to 8 hours, up to 4 hours, and up to 2 hours. In other embodiments, the composition or compositions can contact the body for less than 2 hours, including 10, 20, 30, 40, 50, 60, 70, 80, 90, 100, 110, and 120 minutes and increments in between.

In some embodiments, the TLR agonist and the immune checkpoint modulator, such as a CTLA-4, PDL-1 or PD-1 antagonist, are administered by a thermoreversible hydrogel, either together or in different hydrogel compositions. In other particular embodiments wherein one or more of the immunomodulatory agents contacts the body for a minimal amount of time (e.g. less than 4 hours, such as less than 3, 2, or 1 hour), one of the agents can but need not be provided in a hydrogel composition, and may be administered locally, such as by liquid instillation, as is known in the art. In such embodiments for example, a selective anti-CTLA-4 antagonist antibody can be provided in solution by local administration (in solution, such as by instillation, and the TLR agonist can be provided in a thermoreversible hydrogel formulation or via versa. In another non limited embodiment one of the agents, preferably an immune checkpoint modulator can be administered systemically, while the other is administered by local instillation.

In particular embodiments the TLR agonist and an immune checkpoint modulator are administered in sequence, with or without a washing step in between. One of skill will appreciate that the time which each composition in such methods can be applied to the body cavity can be any of the times described herein. Likewise, a sequence of washing steps of equal or varying duration can be included in such methods between administrations of each composition.

In particular embodiments, the described agents are administered sequentially such that the TLR agonist is administered first and the immune checkpoint modulator is administered second.

In particular embodiments, after the specified period of time, the second administered composition (or last-administered composition in the case of more than two compositions) composition is washed from the internal body cavity. The washing solution can be the same or different from a solution used to wash the first composition from the body cavity.

The described methods locally administer active pharmaceutical agents in one or more compositions that include a gel having reverse thermal gelation properties (a "thermoreversible hydrogel").

In particular embodiments wherein the active agents are administered separately, the thermoreversible hydrogel compositions can be the same. In other embodiments, the thermoreversible hydrogel composition is different in the compositions for administering different active agents. For example, in some embodiments, the thermoreversible hydrogel composition of the first composition degrades more quickly than that of the second composition under physiological conditions. In other embodiments, the thermoreversible hydrogel composition of the second composition degrades more quickly than that of the first composition under physiological conditions.

The gelation properties of the thermoreversible hydrogel composition allow the compositions to be administered in liquid form to the surface of an internal body cavity. Such administration can be by any method known to the art, using any device suitable to apply the subject compositions. For example, methods known to the art of intravesical instillation of an agent can be used to administer the compositions described herein to the surface of an internal body cavity.

As described herein, the "effective amount" of the produced TLR agonist agents and immune checkpoint modulators, such as checkpoint antagonists, include amounts which can provide an anti-cancer effect. In particular, the anti-cancer effect that is provided in the combined treatments is expected to be greater than the effect provided by each treatment individually, such as a non-additive or "synergistic" effect. It will be appreciated that a wide range of dosages, concentrations, and dosage regimens can be developed from the described compositions and methods to provide such anti-cancer effects.

In particular embodiments, the TLR agonist is provided at a concentration of 0.005% (w/v) to 10% (w/v), and particularly 0.01% (w/v) to 5% (w/v), 0.1% (w/v) to 4% (w/v), 0.1% (w/v) to 3% (w/v), and 0.1% (w/v) to 2% (w/v). In such embodiments, the TLR agonist can be any of the TLR agonists described herein, such as the TLR-7 agonist, an imidazoquinolin (amine) or functional derivative thereof.

In preferred embodiment of the present invention, the TLR-7 agonist optionally is embedded in a pharmaceutical composition further comprises at least one polymer, wherein this polymer is preferably selected from chitosan or its derivatives, or from a poly(ethylene oxide)-poly(propylene oxide)-poly(ethylene oxide) copolymer (also termed PEO-PPO-PEO or poloxamer).

In other embodiments, the immune checkpoint modulator is a CTLA-4, PDL-1, or PD-1 inhibitor. In particular embodiments, the CTLA-4 inhibitor can be Ipilimumab or Tremelimuab provided at a concentration of 5 (mg/Kg B·W) to 50 (mg/Kg B·W). In other embodiments, the PDL-1 inhibitor is Atezolizumab, Durvalumab, or Avelumab provided at a concentration of 5 (mg/Kg B·W) to 70 (mg/Kg B·W). In still other embodiments, the PD-1 inhibitor is Pembrolizumab or Nivolumab provided at a concentration of 0.5 (mg/Kg B·W) to 30 (mg/Kg B·W).

Treatment regimens of the described compositions will vary from patient to patents and will depend on the determined efficacy and/or prognosis of the provided treatments. As described above, certain treatment regimens include local administration of both the TLR agonist and immune checkpoint antagonist. In other certain treatment regimens, the TLR agonist is administered locally, while the immune checkpoint modulator is administered systemically. In a particular example of either type of regimen, the active agents can be re-administered at periodic frequencies as described below. In other particular examples of such regimens, the TLR agonist is imiquimod or any derivative thereof in a concentration of 0.1% (w/v) to 5% (w/v) M.

In particular embodiments, the TLR agonist and the immune checkpoint modulator are administered at a frequency of 3, 4, 5, 6, 7, 8, 9, 10, 12, 15, 18, 24, 48, 72 hours, 1 week, 10 days, two weeks, three weeks and up to 1, 2, 3 months, or even longer. In a particular embodiment, the agents are provided concurrently at a frequency of every 3 weeks, for a total of 12 weeks. In further embodiments, the patient is treated with a repetitive regimen that includes a TLR agonist provided in a thermoreversible hydrogel, an optional wash, and local administration of an immune checkpoint inhibitor also formulated in a thermoreversible hydrogel. Each composition is allowed to contact the target tissue for a specified duration of time, such as 10-120 minutes or longer as described above. The regimen is repeated daily, every other day, weekly, or monthly, depending on the determined clinical need of the patient.

Anti-cancer treatment regimens can proceed in tiers or phases or treatment, with the initial phase described as an "induction phase" and which is followed by a "maintenance phase". In such phases of treatment, as well as other, intermediate phases, the compositions described herein can be provided in varying combinations, frequencies of administration, and duration of administration as described above. In particular embodiments, each phase of treatment immediately follows the preceding phase. In other embodiments, each phase of treatment proceeds following a waiting period of days or weeks.

In a particular embodiment, the immune checkpoint modulator is first administered once a week or once every 2 weeks or once every 3 weeks for a period of up to 12 weeks, and the TLR agonist is administered once a week or once every 2 weeks or once every 3 weeks for a period of up to 12 weeks during an induction phase, which is followed by administration of the immune checkpoint modulator antibody once every 3-12 weeks and administration of the TLR agonist once every 1-6 months during a maintenance phase of 12 weeks to 36 months. Other combinations of treatment frequencies and duration are within the skill of the art and are encompassed by the current disclosure.

In particular embodiments, in addition to the methods of treatment described herein, the patient has received, is concurrently receiving, or subsequently will be treated with any of the standard anti-cancer treatment known in the art comprising: chemotherapy, radiation therapy, hormone therapy and surgery.

Additional methods described herein include methods of inhibiting the regrowth of cancer of an internal body cavity in a human subject, the method including administering to a subject in need thereof a therapeutically effective amount of a TLR agonist, and an immune checkpoint modulator. At least one of the TLR agonist and the immune checkpoint modulator, such as an immune checkpoint inhibitor, are provided in a thermo-reversible hydrogel composition comprising chitosan or at least one tri block copolymer having a general formula ABA or BAB copolymer, wherein A is a hydrophilic block and B is a hydrophobic block, thereby inhibiting the regrowth of the cancer of the body cavity. As demonstrated herein, the described methods of treatment can be administered to the subject after a cancer under treatment has been removed or lessened in the subject. In such methods, the described methods can prevent or inhibit the reoccurrence of the cancer, or decrease the rapidity and/or severity of tumor regrowth.

In particular embodiments of the method of inhibition described above, the patient will receive the above-mentioned regimen daily, every other day, weekly, or monthly, subsequent to an initial treatment regimen, and depending on the determined clinical need of the patient.

In particular embodiments of the methods described above, the TLR agonist and checkpoint modulator can be administered simultaneously, individually, repetitively, subsequent to each other or in any combination thereof. Either the TLR agonist or the checkpoint modulator can be administered first followed by any of the mentioned treatment regimens. For example, although in some embodiments, the described dosage regimens can supply the TLR agonist and checkpoint modulator in alternating administrations, in other embodiments, the pattern of administration is not alternating, but rather one or the other active agent can be supplied in more than one period of administration before the administration of the other active agent, which can also be supplied in more than one period of administration.

REFERENCES

1. Johanna Holldack, BioSpace (Oct. 31, 2011), available online at biospace.com/article/releases/telormedix-announces-promising-tmx-202-preclinical-results-for-skin-cancer-treatment-/
2. Darvin Me. et al., J Biomed Opt. 2016 May 31; 21(5): 55004.
3. Ursu, R et al (2015). Cancer science. 106.10.1111/cas.12724
4. Thompson, John A. et al. Clin Genitourinary Cancer, Vol 7, Issue 3, E58-E65
5. Zhu D, et al. Natural products chemistry & research. 2016; 3(4):e113.
6. Cynthia L. Gay, et al, The J of Infect Dis, 215(11). 1725-1733, 2017.
7. Korde et al. Haematologica 99.6 (2014): e81-e83. PMC. Web. 24 Oct. 2017.
8. Tolcher et al., Clin Cancer Res Sep. 15 2017 (23) (18) 5349-5357
9. Diab, A et al. (2016) Japanese Society of Medical Oncology. 27.
10. 1093/annonc/mdw378.08.

10. Infante J. et al., Abstract CT027: Cancer Res Jul. 15 2016 (76) (14Supplement)
11. Attarwala H. Journal of Young Pharmacists: JYP. 2010; 2(3):332-336.
12. Ribas A. et al., Oncologist. 2007 July; 12(7):873-83
13. NIH Clinical Trials clinicaltrials.gov/ct2/show/NCT01714739
14. NIH Clinical Trials clinicaltrials.gov/ct2/show/NCT03250832.
15. Donin, N. M., Lenis, A. T., et al (2017). Immunotherapy for the treatment of urothelial carcinoma. *The Journal of urology,* 197(1), 14-22.

The following examples are provided to illustrate certain particular features and/or embodiments. These examples should not be construed to limit the disclosure to the particular features or embodiments described.

EXAMPLES

Example 1: Checkpoint Inhibition with Systemic Anti-PD-L1 Combined with Intravesical TMX-101 Decreases Tumor Burden in a Mouse Model of Urothelial Carcinoma Methods Materials for use in this example are commercially available. Unless otherwise indicated, the methods follow standard procedures. Certain related materials and methods are as described in Donin et al., Urol Oncol. 2017 February; 35(2):39.el-39; Donin, N. M., Lenis, A. T., Holden, S., Drakaki, A., Pantuck, A., Belldegrun, A., & Chamie, K. (2017). Immunotherapy for the treatment of urothelial carcinoma. *The Journal of urology,* 197(1), 14-22; and Lenis et al., Journal of Urology, Vol. 197, No. 4S, Supplement, Tuesday, May 16, 2017, e1313

Tumor Implantation (Day 0)

32 female C57Bl/6 mice aged 6-8 weeks were used in the study Bladders were pre-treated with 0.1% poly-L-lysine for 20 minutes. Following pretreatment, $10^6$ MB49 tumor cells instilled into the bladder in 50% MatriGel for 1 hour.

Treatments (Day 3/4, 6/7, and 9)

Mice were treated with one of four regimens: 1) vehicle+isotype, 2) TMX-101+isotype, 3) Vehicle+anti-PD-L1, or 4) combination therapy (TMX-101+anti-PD-L1) on Days 3, 6, and 9 following tumor implantation.

Intravesical TMX-101 was given on Days 3, 6, and 9 for 20 minutes. aPD-L1 was given via intraperitoneal (ip) injection on Days 4 and 7.

Outcomes (Day 11)

Figure 1:
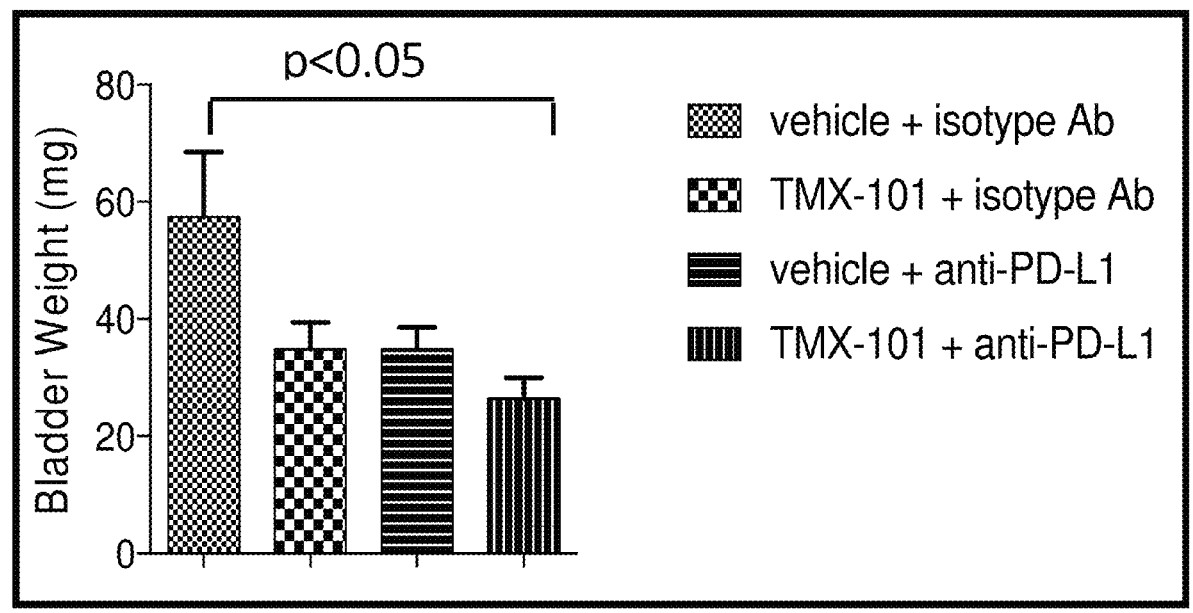
FIG. 1 is a chart showing the Mean+/−SEM of bladder weight in the indicated treatment and control groups. N=6-9 mice. Particular values are shown in Table 1.
Figure 2:
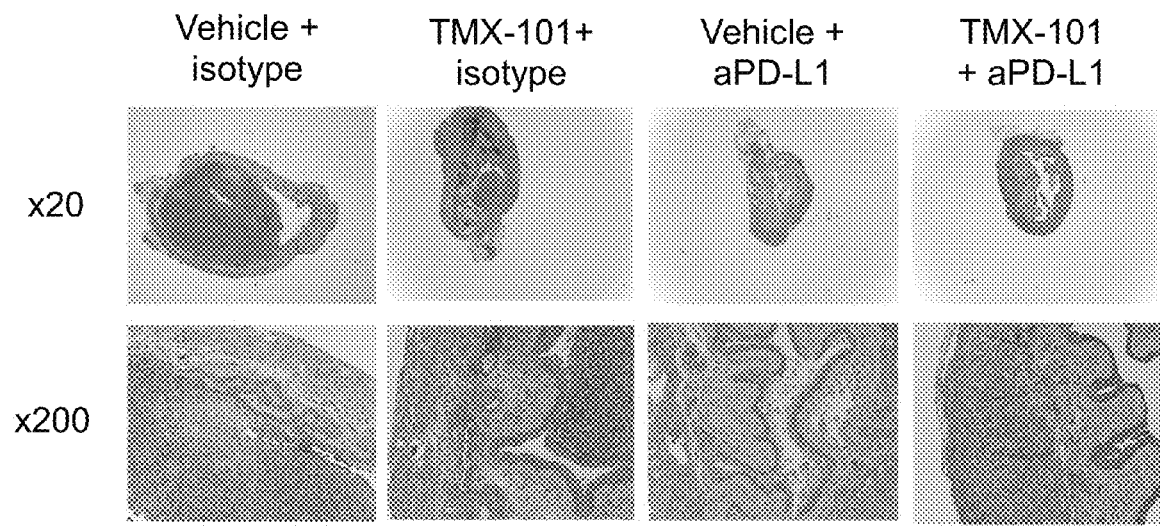
FIG. 2 shows representative H&E sections of bladder showing reduction in tumor burden in combination treated mice compared with either treatment alone or controls. Mice were treated with one of four regimens: 1) vehicle+isotype, 2) TMX-101+isotype, 3) Vehicle+anti-PD-L, or 4) combination therapy (TMX-101+anti-PD-L1) on Days 3, 6, and 9 following tumor implantation. Top panels show 20× magnification, bottom panels show 200× magnification.
Figure 3A:
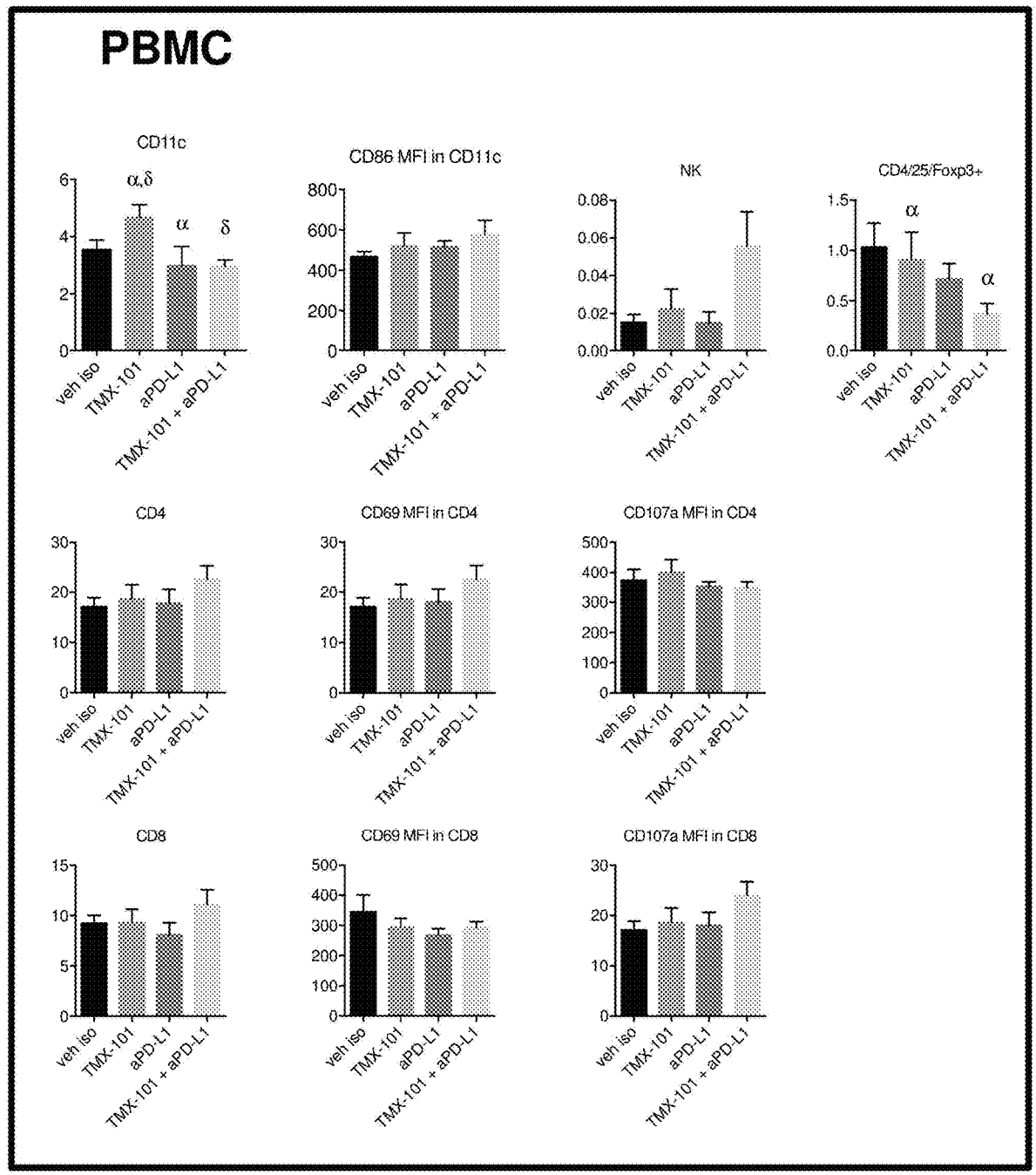
FIGS. 3A-3C show FACS analysis of PBMC (FIG. 3A), spleen (FIG. 3B), and pooled regional lymph nodes (FIG.
Figure 3B:
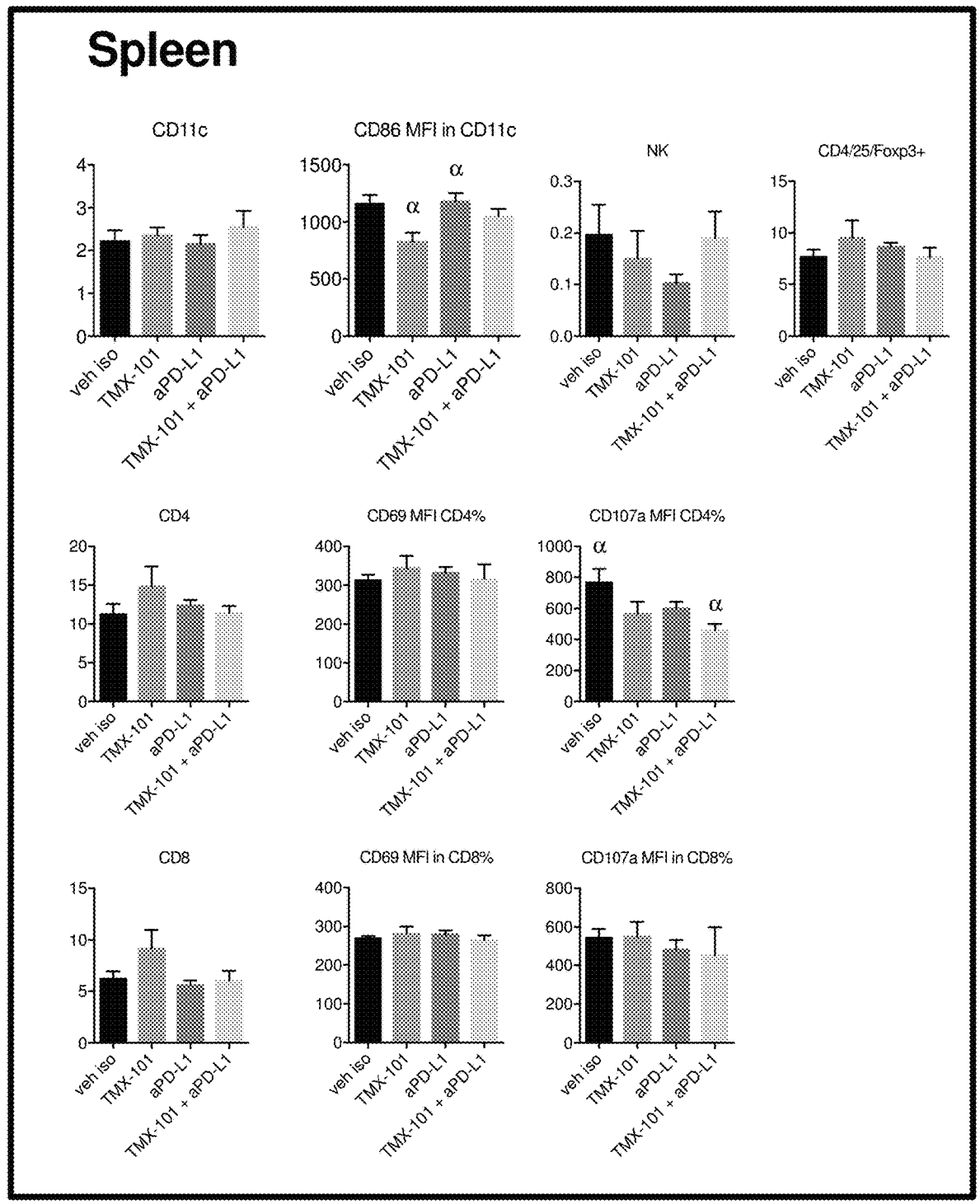
Figure 3C:
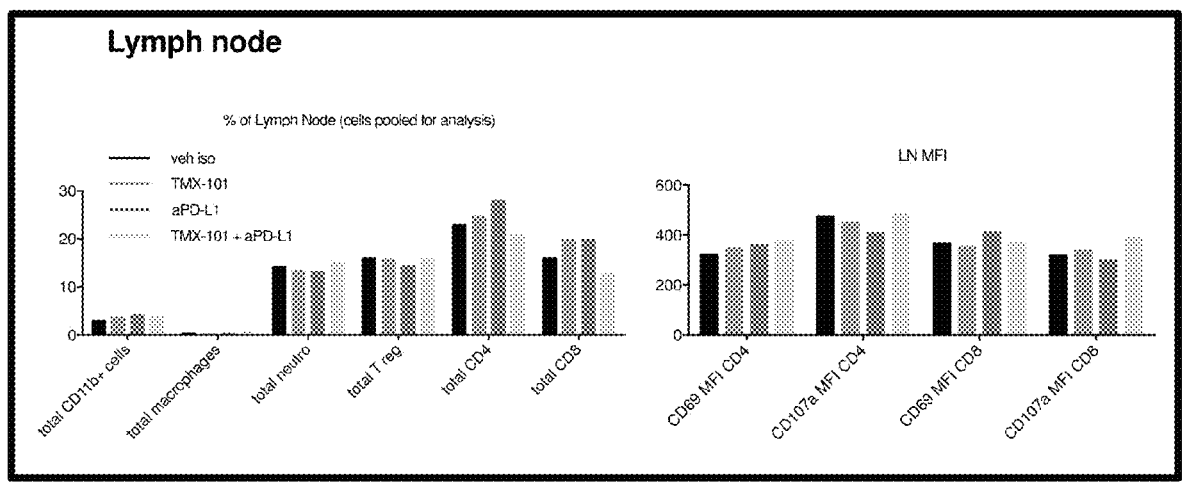

Bladder weight was used as a measure of tumor burden and compared using the Kruskal-Wallis test (FIG. 1). Histologic analysis of bladder was performed (FIG. 2). Fluorescence activated cell sorting (FACS) analysis of peripheral blood mononuclear cells (PBMC), spleen, and regional lymph nodes was performed for T-cell populations (FIG. 3A-3C).

Results

As shown in FIG. 1 and in Table 1, below, combination TMX-101 and anti-PD-L1 reduced bladder weight significantly more than mice treated with either treatment alone and more than control treated mice (p<0.05).

TABLE 1

Bladder weight of treated mice

| Group | Bladder weight, mg (SD) |
| --- | --- |
| Vehicle + isotype Ab | 57.4 (11.1) |
| TMX-101 + isotype Ab | 34.8 (4.7) |
| Vehicle + aPD-L1 | 34.8 (3.8) |
| TMX-101 + aPD-L1 | 26.4 (3.5) |

The reduction in tumor burden following the combination treatment as indicated by bladder weight is also illustrated in FIG. 2, which shows representative H&E sections of bladder showing reduction in tumor burden in combination treated mice compared with either treatment alone or controls. Measurement of T-cell populations in treated animals indicated a trend towards an increase in T-cell activation and decrease in regulatory T-cells (FIGS. 3A-3C).

Conclusion

Combination TMX-101 and aPD-L1 significantly reduced bladder weight, a marker of tumor burden, more than either treatment alone in a mouse model of UC.

Example 2: Checkpoint Inhibition with Intravesical Anti-PD-1 Combined with Intravesical Treatment of TLR7 Agonist Formulation Decreases Tumor Burden in a Mouse Model of Urothelial Cancer Methods RTGel used for this example is TC-3 (contains 27% Poloxamer 407, 0.2% HPMC and 1% PEG 400). TLR7 agonist formulation for intravesical administration (Vesimune/TMX-101/UGN-201) used contains: 160 gr/L Poloxamer P407, 50 gr/L Cyclodextrin, 10.2 gr/L Lactic acid (50%) and 1 gr/L Imiquimod. Vehicle formulation used contains: 160 gr/L Poloxamer P407, 50 gr/L Cyclodextrin, 10.2 gr/L and Lactic acid (50%). Mouse anti-PD-1 antibody (RMP1-14) and isotype antibody (rat IgG2a Isotype control) were purchased from BioXCell.

Tumor Implantation (Day 0):

Female C3H/HEJ mice were anaesthetized and bladders catheterized. Bladder pretreatment was done with acid-base (0.1 N HCl for 15 seconds followed by 0.1N NaOH for additional 15 seconds). Bladder was flushed with PBS and $2\times10^{\wedge}$MBT-2 mouse bladder cancer cells were instilled into the bladder for 45 minutes.

Treatments (Day 5, 10 and 15):

Treatments were given on days 5, 10 and 15 following tumor implantations and consisted of 2 treatments. The first treatment of intravesical TLR7 agonist formulation or Vehicle was given for 20 minutes and was followed by anti-PD1 or isotype (400 µg). The antibodies were administrated via one of three methods: 1. Intravesical instillation in RTGel. 2. Intravesical instillation in solution for 60 minutes. 3. Intraperitoneal (IP) injection. Some animals served as control groups (treated with Vehicle+ Isotype, while other groups were treated with only one active formulation (TLR7 agonist formulation+ Isotype or Vehicle+anti-PD1), or with the combination (TLR7 agonist formulation+anti-PD1).

Outcomes:

Following treatment completion (days 20-21), animals were imaged by MRI and bladder tumor volume was evaluated. Animal survival was further monitored.

Results

Combination of intravesical TLR7 agonist and with anti-PD1 resulted in lower median tumor volume in comparison to control and single treatments (FIG. 4A-4C). The median tumor volume was the lowest when the intravesical anti-PD1 was administered in RTGel as part of the combined treatment (FIG. 4A), in comparison to intravesical anti-PD1 in solution (FIG. 4B), or when given via the IP route (FIG. 4C). Animals treated with the combined treatment showed higher survival rate in comparison to control treated mice for both intravesical anti-PD1 in RTGel group (p=0.0532) and via the IP route (p<0.005, FIG. 5A-5C).

Conclusions

Combination therapy of intravesical TLR7 agonist and intravesical anti-PD1 in RTGel reduced tumor burden as demonstrated by the decreased tumor volume and the increased survival rate. Although not significantly better than combination therapy with systemic anti-PD1 (via the IP route), this local administration of immune check inhibitors is expected to result in considerably less systemic toxicity associated with this class of molecules when systemically administered, and accordingly indicates a distinct clinical advantage over the systemic administration.

Example 3: Checkpoint Inhibition with Intravesical Anti-CTLA4 Combined with Intravesical Treatment of TLR7 Agonist Formulation Decreases Tumor Burden in a Mouse Model of Urothelial Cancer Methods:

RTGel used for this example is TC-3 (contains 27% Poloxamer 407, 0.2% HPMC and 1% PEG 400). TLR7 agonist formulation for intravesical administration (Vesimune/TMX-101/UGN-201) used contains: 160 gr/L Poloxamer P407, 50 gr/L Cyclodextrin, 10.2 gr/L Lactic acid (50%) and 1 gr/L Imiquimod. Vehicle formulation used contains: 160 gr/L Poloxamer P407, 50 gr/L Cyclodextrin, 10.2 gr/L and Lactic acid (50%). Mouse anti-CTLA4 antibody (clone 9H10) and isotype antibody (polyclonal Syrian hamster IgG) were purchased from BioXCell.

Intravesical Tumor Implantation (Day 0):

Female C3H/HEJ mice were anaesthetized and bladders catheterized. Bladder pretreatment was done with acid-base (0.1 N HCl for 15 seconds followed by 0.1N NaOH for additional 15 seconds). Bladder was flushed with PBS and 2×10^MBT-2 mouse bladder cancer cells were instilled into the bladder for 45 minutes.

Treatments (Day 5, 10 and 15):

Treatments were given on days 5, 10 and 15 following tumor implantations and consisted of 2 treatments. The first treatment of intravesical TLR7 agonist formulation or Vehicle was given for 20 minutes and was followed by anti-CTLA4 or isotype (400 µg). The antibodies were administrated via one of three methods: 1. Intravesical instillation in RTGel. 2. Intravesical instillation in solution for 60 minutes. 3. Intraperitoneal (IP) injection. Some animals served as control groups (treated with Vehicle+ Isotype or water for injection (WFI), while other groups were treated with only one active formulation (TLR7 agonist formulation+ Isotype or Vehicle+anti-CTLA4), or with the combination (TLR7 agonist formulation+anti-CTLA4).

Re-Challenge with Tumor Cells

Surviving mice were re-challenged with subcutaneous (SC) injection of 1×10^ MBT-2 cells into the right flank (Day 78-following initial tumor cells implantation in the bladder).

Outcomes:

Following treatment completion (days 18 to 21), animals were imaged by MRI and bladder tumor volume was evaluated. Animal survival was monitored, and Fluorescence activated cell sorting (FACS) analysis of regional lymph nodes was performed for major T cell populations. Tumor volume in mice that were re-challenged subcutaneously was measured 3 times a week.

Results

Combination of intravesical TLR7 agonist and intravesical anti-CTLA4 in RTGel resulted in decreased median tumor volume compared to control and single treatments (FIG. 6A-6B). When the intravesical anti-CTLA4 was administered in solution, median tumor volume was not different than that of the control, while when administered via the IP route, median tumor volume was smaller than the controls but to a lesser extent compared to intravesical anti-CTLA4 in RTGel (FIG. 7A-7B).

Animals treated with the combined treatment showed significantly higher survival rate in comparison to control treated mice when intravesical anti-CTLA4 was delivered in RTGel or via the IP route (FIGS. 8A-8C), but not when anti-CTLA4 was delivered intravesically in solution (FIG. 8B). When anti-CTLA-4 was delivered in RTGel, significantly higher survival rates were observed also in comparison to individual the treatments.

Assessment of major T cell populations show an increase in the number of activated T effectors cells and a decrease in the number of T regulatory cells in mice treated with intravesical TLR7 agonist and anti-CTLA4 in RTGel (FIGS. 9A-9C).

Re-challenge of mice treated with intravesical TLR7 agonist and anti-CTLA4 in RTGel resulted in the development of smaller tumors when compared to mice treated with TLR7 agonist alone and to naïve controls (FIG. 10).

Conclusions:

Combination therapy of intravesical TLR7 agonist and intravesical anti-CTLA4 in RTGel reduced tumor burden as demonstrated by the decreased tumor volume and the increased survival rate. Following this treatment, the effect on major T cell populations, normally affected by immune check inhibition was reversed, supporting the enhanced anti-tumoral function. This treatment also conferred adaptive immunity to re-challenge suggesting immunological memory.

Overall, the intravesical TLR7 agonist and checkpoint modulators provided in RTGel proves advantageous over the systemic or intravesical solution administration routes. The described immunotherapy provided in the RTGel is not expected to diffuse away from a body cavity or cause systemic toxicity, and provides a new means of controlling the delivery and the activity of immune checkpoint modulators in order to treat cancer of an internal body cavity.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of treatment for a cancer of an internal body cavity in a human subject, the method comprising:
   administering to a subject in need thereof a therapeutically effective amount of:
   (a) a TLR agonist comprising an imidazoquinolin amine provided at a concentration of 0.005% (w/v) to 10% (w/v), and
   (b) an immune checkpoint antagonist comprising an anti-CTLA-4 antibody, wherein at least one of the TLR agonist and the immune checkpoint antagonist are provided in a thermoreversible hydrogel composition comprising a poloxamer, and wherein at least (a) is administered locally into the internal body cavity, thereby treating the cancer of the body cavity.

2. The method of claim 1 wherein the immune checkpoint antagonist is an anti-CTLA4 antibody selected from the group consisting of: Ipilimumab (Yervoy), Tremelimumab (CP-675,206), AGEN-1884, AGEN-2041 (AGEN-1181), ADU-1604, AK 104, BCD-145, BMS-986249, CBT-509, ATOR 1144, and ATOR-1015.

3. The method of claim 1, wherein the poloxamer has an average molecular weight of 8500-16000DA, inclusive.

4. The method of claim 1, wherein the Poloxamer comprises Poloxamer 407, Poloxamer 188, Poloxamer 124, Poloxamer 237, or Poloxamer 338 or combination thereof.

5. The method of claim 1, wherein the cancer is selected from the group consisting of bladder cancer, urinary tract cancer, upper urinary tract cancer, renal cancer, gastrointestinal cancer, colon cancer, rectal cancer, and female reproductive system cancer.

6. The method of claim 1, wherein the thermoreversible hydrogel composition further comprises a mucoadhesive polymer.

7. The method of claim 1, wherein the thermoreversible hydrogel composition comprises 15% (w/w)-40% (w/w) poloxamer 407.

8. The method of claim 1 wherein the anti-CTLA-4 antibody is Ipilimumab or Tremelimuab provided at a concentration 1 (mg/Kg B·W) to 50 (mg/Kg B·W).

9. The method of claim 1, wherein the TLR agonist is administered intravesically.

10. The method of claim 1, wherein the TLR agonist and the immune checkpoint antagonist modulator are provided in the thermoreversible hydrogel intravesically into the internal body cavity.

11. The method of claim 1, wherein the TLR agonist and immune checkpoint antagonist modulators are administered simultaneously, repetitively, in sequence or in any combination thereof.

12. A method for inhibiting re-growth of a cancer of an internal body cavity in a human subject, the method comprising:

administering to a subject in need thereof a therapeutically effective amount of:

a TLR agonist comprising an imidazoquinolin amine provided at a concentration of 0.005% (w/v) to 10% (w/v), and an immune checkpoint antagonist comprising an anti-CTLA-4 antibody, wherein at least one of the TLR agonist and the immune checkpoint antagonist are provided in a thermoreversible hydrogel composition comprising a poloxamer, and wherein the TLR agonist and immune checkpoint antagonist are administered to the subject subsequent to a treatment for the cancer which removed or decreased the amount of the cancer in the subject, thereby inhibiting the regrowth cancer of the body cavity.

13. The method of claim 1, further comprising a wash of the internal body cavity between (a) and (b).

14. The method of claim 1, wherein the imidazoquinoline amine is imiquimod.

15. The method of claim 12, wherein the imidazoquinolin amine is imiquimod.

* * * * *